(12) United States Patent
Bufano et al.

(10) Patent No.: US 8,293,173 B2
(45) Date of Patent: Oct. 23, 2012

(54) ELECTRON BEAM STERILIZATION APPARATUS

(75) Inventors: Michael Lawrence Bufano, Belmont, MA (US); Steven Raymond Walther, Andover, MA (US); Peter F. Hays, Medford, MA (US); William Frederick Thomson, Milford, NH (US); Arthur Wayne Sommerstein, Marblehead, MA (US); Gerald Martin Friedman, New Ipswich, MA (US); P. Michael Fletcher, Chelmsford, MA (US); Stephen Whittaker Into, Harvard, MA (US); Anne Testoni, Bolton, MA (US); Brian S. Phillips, Sherborn, MA (US)

(73) Assignee: Hitachi Zosen Corporation, Suminoe-Ku (JP)

( * ) Notice: Subject to any disclaimer, the term of this patent is extended or adjusted under 35 U.S.C. 154(b) by 3 days.

(21) Appl. No.: 12/841,560

(22) Filed: Jul. 22, 2010

(65) Prior Publication Data
US 2011/0012032 A1    Jan. 20, 2011

Related U.S. Application Data

(63) Continuation-in-part of application No. 12/770,083, filed on Apr. 29, 2010.

(60) Provisional application No. 61/227,566, filed on Jul. 22, 2009, provisional application No. 61/288,569, filed on Dec. 21, 2009, provisional application No. 61/174,061, filed on Apr. 30, 2009.

(51) Int. Cl.
*A61L 2/08* (2006.01)
*B65B 55/08* (2006.01)

(52) U.S. Cl. ............... 422/22; 250/492.3; 250/493.1; 250/492.1; 315/111.81; 315/111.91

(58) Field of Classification Search ............ 250/492.3, 250/493.1, 492.1; 315/111.81, 111.91; 422/22; 53/425
See application file for complete search history.

(56) References Cited

U.S. PATENT DOCUMENTS

| | | |
|---|---|---|
| 3,780,308 A | 12/1973 | Nablo |
| 4,252,413 A | 2/1981 | Nablo |
| 5,962,995 A | 10/1999 | Avnery |
| 6,139,796 A | 10/2000 | Kristiansson et al. |

(Continued)

FOREIGN PATENT DOCUMENTS
EP    1 956 608 A1    8/2008
(Continued)

OTHER PUBLICATIONS

Bufano, et al., Ebeam Sterilization Apparatus, U.S. Appl. No. 12/770,083, filed Apr. 29, 2010, 73 pages.

(Continued)

*Primary Examiner* — Nikita Wells
(74) *Attorney, Agent, or Firm* — Ropes & Gray LLP

(57) ABSTRACT

Improved electron beam sterilization apparatus and shielding techniques for use in are provided. A controller modulates an electron beam when sterilizing an interior to an object to ensure that adequate dose is received. Sterilization carousels are configured with input/discharge feeds to reduce the possibility of humans being exposed to dangerous levels of radiation. The system reduces the amount of shielding required to thereby lower cost of installation.

20 Claims, 30 Drawing Sheets

U.S. PATENT DOCUMENTS

| | | | |
|---|---|---|---|
| 6,221,216 | B1 | 4/2001 | Nablo et al. |
| 6,407,492 | B1 | 6/2002 | Avnery et al. |
| 6,624,229 | B1 | 9/2003 | Riestenpatt et al. |
| 6,674,229 | B2 | 1/2004 | Avnery et al. |
| 6,833,551 | B2 | 12/2004 | Avnery |
| 6,919,570 | B2 | 7/2005 | Avnery |
| 7,759,661 | B2 * | 7/2010 | Avnery ............ 250/493.1 |
| 7,832,185 | B2 * | 11/2010 | Mastio et al. ............ 53/426 |
| 2007/0283667 | A1 | 12/2007 | Kristiansson et al. |
| 2008/0073549 | A1 | 3/2008 | Avnery |
| 2008/0138243 | A1 | 6/2008 | Kristiansson et al. |
| 2009/0045350 | A1 | 2/2009 | Humele et al. |
| 2011/0012030 | A1 * | 1/2011 | Bufano et al. ............ 250/492.3 |

FOREIGN PATENT DOCUMENTS

| | | |
|---|---|---|
| EP | 2 161 202 A1 | 8/2008 |
| WO | WO 01/04924 A1 | 1/2001 |
| WO | WO 02/061464 A1 | 8/2002 |

OTHER PUBLICATIONS

Bufano, et al., Ebeam Sterilization Apparatus, U.S. Appl. No. 61/227,566, filed Jul. 22, 2009, 24 pages.

Thomson, et al., Shielding for Electron Beam Sterilization, U.S. Appl. No. 61/288,569, filed Dec. 21, 2009, 44 pages.

Walther, et al., Ebeam Sterilization of Deep Hole Targets, U.S. Appl. No. 61/174,061, filed Apr. 30, 2009, 16 pages.

Carretero Botella, N., et al., PCT Notification of Transmittal of the International Search Report and the Written Opinion of the International Searching Authority, or the Declaration, International Application No. PCT/US2010/002071, International Filing Date: Jul. 22, 2010, Date of Document Mailing: Nov. 4, 2010, 14 pages, European Patent Office, Rijswijk, Netherlands.

Cleghorn, D.A., et al., Sterilization of Plastic Containers Using Electron Beam Irradiation Directed Through the Opening, The Society for Applied Microbiology, Journal of Applied Microbiology, vol. 93, Issue 6, pp. 937-943, Aug. 5, 2002.

* cited by examiner

ELECTRON BEAM STERILIZATION APPARATUS

RELATED APPLICATIONS

The present invention is a Continuation in Part of U.S. patent application Ser. No. 12/770,083, filed Apr. 29, 2010, by Bufano et al for EBEAM STERILIZATION APPARATUS, which claims priority to U.S. Provisional Application No. 61/227,566, filed on Jul. 22, 2009 by Bufano et al., for EBEAM STERILIZATION APPARATUS, and also claims priority to U.S. Provisional Application No. 61/288,569, filed on Dec. 21, 2009 by Thomson et al., for SHIELDING FOR ELECTRON BEAM STERILIZATION, and also claims priority to U.S. Provisional Application No. 61/174,061, filed on Apr. 30, 2009 by Walther et al., for EBEAM STERILIZATION OF DEEP HOLE TARGETS, the contents of each of these applications is hereby incorporated by reference.

FIELD OF THE INVENTION

This invention relates to electron beam (ebeam) sterilization, and more specifically to an electron beam sterilization of and electron beam sterilization system designs for aseptic filling applications for bottles and other packaging containers used for packaging food, beverages, pharmaceutical, ophthalmic and other products.

BACKGROUND OF THE INVENTION

It is well known in the art that many packaged products including food, beverage, pharmaceutical, ophthalmic, and medical products are produced using microbiologically clean (i.e. sterile) packaging conditions in order to improve safety, shelf life, and quality of the end product. Processes using sterile packaging conditions may be referred to as aseptic packaging, extended shelf life (ESL) packaging, shelf stable packaging and/or ultra clean packaging. The level of sterility (i.e. degree to which packaging surfaces and processing conditions are free of microbes) depends on many conditions including the product being packaged (e.g., pH level of product), varying state and country regulations, and the intended shelf life of the packaged product. Sterile packaging conditions are achieved by sterilizing or disinfecting packaging material, sterilizing or pasteurizing the product to be packaged, filling the package with the product in a sterile environment, and sealing the package in the sterile environment.

Packaging sterilization is typically accomplished with heat or chemical based sterilants. These traditional methods of sterilization have noted disadvantages including, but not limited to:

- High heat requires more thermally resistant packaging designs which are typically heavier and more expensive, and less environmentally sustainable
- High heat requires higher energy consumption and costs
- Chemicals are expensive and difficult and dangerous to maintain onsite
- Heat and chemical based sterilization systems are complicated and present difficulties in terms of maintaining sterility
- Chemical based sterilants may need to be removed with water, creating added expense and environmental pollution
- Chemical based sterilants may leave residual traces on packaging material that could potentially contaminate packaged product.

It is well known in the art that electron beams are utilized for sterilization (disinfection/decontamination) of packaging materials, such as flexible packaging plastic films, caps and closures, plastic and glass cups and jars, preformed pouches with or without spouts, preformed plastic bags with or without spouts, bottles, cans, and/or paper board containers. A number of noted disadvantages arise in the use of electron beams for sterilization of packaging materials. A first noted disadvantage in such sterilization is that maintaining adequate (sufficient/uniform) electron beam dose may be difficult in modern production environments. Illustratively, when sterilizing the interior of bottles or other packaging materials, an appropriate dose is required to ensure that sterilization occurs. Should the dose received exceed an upper threshold, undesirable effects may occur to the packaging materials. Similarly, should the dose fail to exceed a minimum threshold, incomplete sterilization may occur, thereby resulting in contamination of the packaged product. In an exemplary bottle sterilization environment, if a bottle is moved relative to an electron beam emitter, portions of the interior the bottle may receive excessive dosage whereas other regions may receive doses outside of an acceptable range. It is thus desirous to ensure that the dose along the entire interior region falls within an acceptable range to ensure proper sterilization with no side affects (i.e., maintaining dose uniformity within an acceptable range). Beyond the bottle illustration, the challenge of maintaining dose uniformity exists for all three dimensional products.

A further noted disadvantage of the use of electron beams for sterilization is that they generate x-ray radiation as a byproduct. Electron beams and these byproduct x-rays, as forms of ionizing radiation, are hazardous (i.e., carcinogenous), can cause tissue damage and as such there exist government regulations and manufacturing best practices that limit the amount of radiation workers can be exposed to during a typical operation and/or maintenance. As such, it is necessary to utilize appropriate shielding for electron beam processes and associated apparatus in a production environment to prevent undesired human exposure to ionizing radiation. Shielding is typically achieved by utilizing some thickness of a material that is incapable of being penetrated by electron beam or x-ray radiation, e.g., lead, and utilizing an appropriate material handling scheme that enables continual or intermittent transport of material into, through, and out of the electron beam process area while keeping ionizing radiation entering the operating area below a threshold. The shielding material used may be coated with one or more additional layers of differing materials to improve resilience, and/or maintain sanitary operating conditions, and/or to protect the electron beam blocking material. The material handling system may incorporate a range of configurations and structures including, labyrinth paths, change in elevation, shutter doors, baffles to improve the shielding efficiency and reduce the overall size and expense of shielding systems.

Certain prior art shielding systems utilize fully shielded rooms in which the sterilization process occurs. In such environments, human operators do not enter the production space during sterilization operations. A noted disadvantage of creating shielded rooms is that the size of a production room may be significant, thereby requiring substantial costs in procuring materials to create the shielded room.

Certain techniques have been developed to reduce the size and material required to produce effective shielding for production environments that utilize web based materials. For example, U.S. Pat. No. 4,252,413, entitled METHOD OF AND APPARATUS FOR SHIELDING INERT-ZONE ELECTRON IRRADIATION OF MOVING WEB MATERI- ALS, the contents of which are hereby incorporated by reference, describes one technique for shielding in a web based material environment. However, a noted disadvantage of such systems is that they are not suitable for use in non-web based environments, e.g. for sterilization of liquid packaging containers, such as bottles or cups.

Exemplary techniques for sterilization are taught in U.S. Pat. No. 6,407,492, entitled ELECTRON BEAM ACCELERATOR, U.S. Pat. No. 6,833,551, entitled ELECTRON BEAM IRRADIATION APPARATUS and U.S. Pat. No. 7,759,661, entitled ELECTRON BEAM EMITTER, the contents of such patents and patent application are hereby incorporated by reference. However, these techniques include a number of noted disadvantages. For example, they fail to provide support to correct the intermittent interruption of electron beams by, e.g., arcs, nor do they provide the ability to continue operations when a single emitter fails. Further, they fail to control dose uniformity for irregularly shaped geometries.

SUMMARY OF THE INVENTION

The present invention overcomes the disadvantages of the prior art by providing a system and method for open mouth container sterilization that ensures that the electron beam dose delivered falls within an appropriate range on the entirety of the interior of the object being sterilized. One or more sensors may monitor the electron beam dose and are operatively interconnected with a controller. A control system modulates the electron beam to ensure that appropriate dose is delivered. The control system may modify a speed at which the object being sterilized is raised/lowered around a nozzle of an electron beam emitter to ensure that an appropriate dose is received. The control system monitors electron beam performance and coordinates system recovery actions in the event of electron beam malfunction. Further, one or more additional electron beam emitters may be configured to sterilize the exterior of the object as its interior is being sterilized with the control system similarly coordinating operation. Alternatively, a single electron beam maybe used to sterilize the interior of the object and sufficient exterior surfaces to maintain sterile filling conditions. Once sterilized, an electron beam may also be used to sufficiently maintain sterility of the interior and exterior surfaces until the object is fully transferred to the sterile zone of the filling system.

The present invention further provides a system and method for improved shielding for electron beam sterilization. A sterilization carousel comprising a plurality of electron beam emitters is operatively interconnected with one or more power supplies. Each electron beam emitter is configured to provide a sufficient dose to a bottle as a nozzle of the electron beam emitter is inserted into the bottle. The sterilization carousel is appropriately shielded and is operatively connected with an input/discharge feed apparatus that is also shielded in a manner to require any x-rays created in the electron beam process zone to intercept the shielding at least three times before they reach an unshielded portion of the apparatus. The input/discharge feed mechanism may comprise a linear feed, an enclosed labyrinth feed, a dual labyrinth feed, and/or the carousels utilizing baffles in accordance with various embodiments of the present invention.

The present invention further provides a system and method for sterilization of deep hole targets that utilizes variations in gas mixtures to improve electron beam performance. Illustratively, a light gas is utilized that completely fills an interior of an object to create a uniform gaseous environment to improve electron beam performance of deep hole targets.

BRIEF DESCRIPTION OF THE DRAWINGS

The advantages of the invention may be better understood by referring to the following description in conjunction with the accompanying drawings in which like reference numerals indicate identical or functionally similar elements.

DESCRIPTION OF PREFERRED EMBODIMENTS

A. Electron Beam Sterilization of Bottles

Figure 1A:
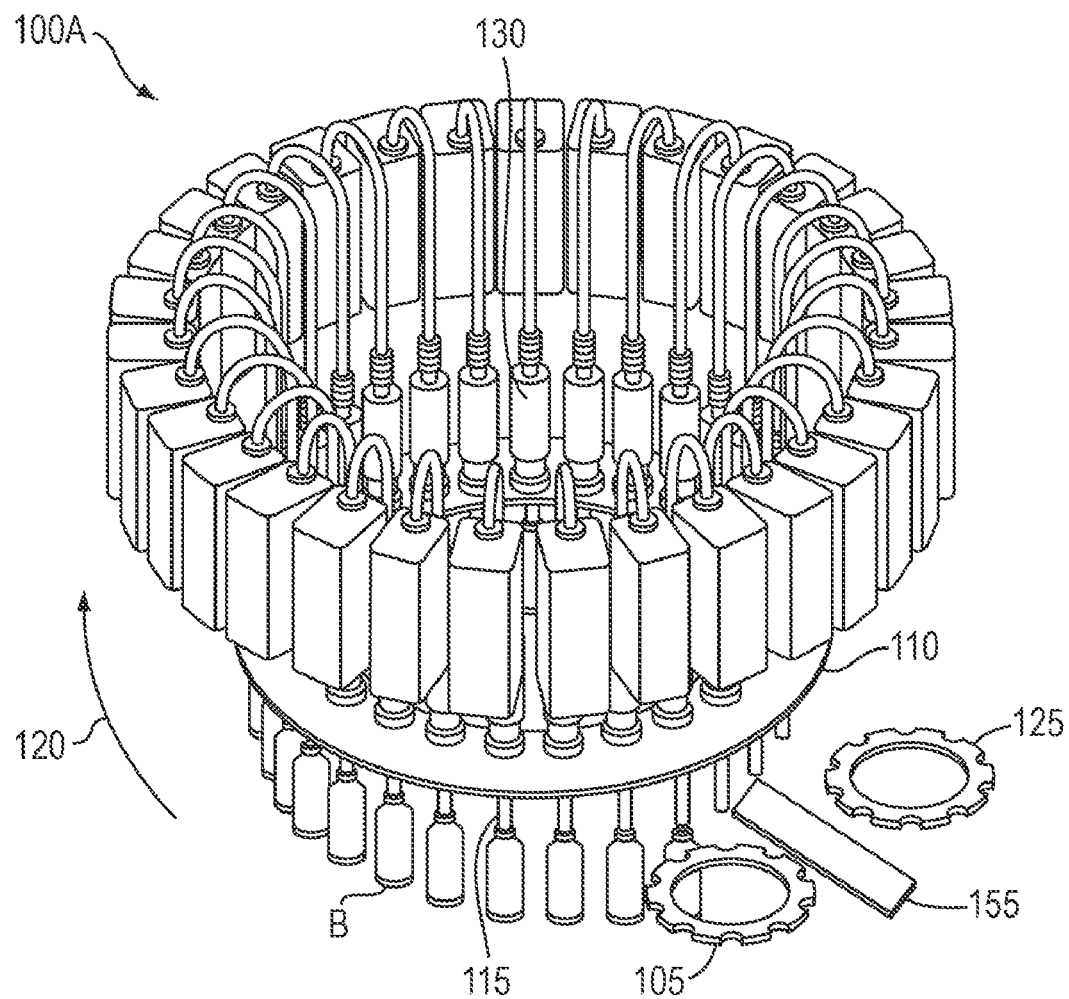
FIG. 1A is a diagrammatic view of an exemplary ebeam sterilization apparatus in accordance with an illustrative embodiment of the present invention.

FIG. 1A is a diagrammatic view of an exemplary electron beam sterilization apparatus 100A in accordance with an illustrative embodiment of the present invention. The apparatus 100A includes an infeed transfer wheel 105, onto which a succession of bottles B is placed by a loader (not shown) and suspended by grippers securing the bottle from either above or below the neck of the bottle. It should be noted that grippers are described in an exemplary embodiment. In alternative embodiments, other techniques may be utilized for transporting bottles. Such alternative techniques may include, e.g., conveyors, vacuum systems, etc. As such, the description of grippers should be taken as exemplary only. The bottles are transferred therefrom to the grippers 115 of a sterilization carousel 110. As the carousel 110 rotates in the direction indicated by arrow 120, the bottles are processed and transported in succession to a discharge wheel 125 which offloads them into a sterile zone in which downstream processing steps, such as a filling and capping (not shown) take place.

Figure 2A:
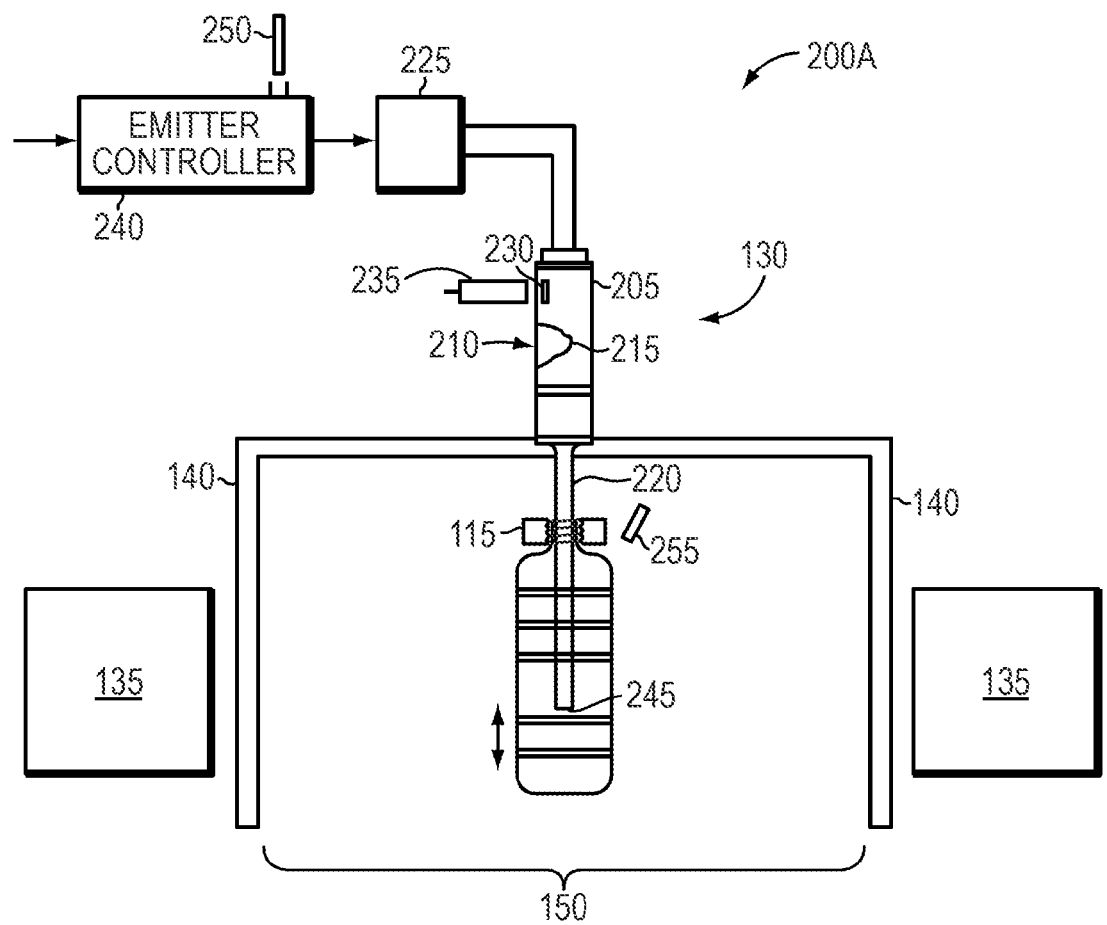
FIG. 2A is a side elevational view on a larger scale showing a portion of the exemplary electron beam sterilization apparatus in greater detail in accordance with an illustrative embodiment of the present invention.

Illustratively, positioned above each bottle gripper 115 is an electron beam emitter 130. FIG. 2A is a side elevational view of an exemplary electron beam emitter 130 environment 200A in accordance with an illustrative embodiment of the present invention. As shown in FIG. 2A, each emitter 130 includes a housing 205 defining a vacuum chamber 210 containing an electron beam generator 215. The housing 205 is formed with an elongated dependent nozzle 220 which is narrow enough to fit into the finish of the bottles B and which is long enough to extend into the bottles. An electron beam window 245 is present at the lower end of each nozzle. It should be noted that the description of exemplary electron beam emitter 130 is illustrative only and that in alternative embodiments, emitter 130 may contain differing and/or additional components. As such, the description herein should be viewed as exemplary only.

As the carousel 110 rotates, the bottle grippers 115 thereof are lifted progressively so that the bottles B are gradually raised around the emitter nozzles 220 to achieve a desired amount of nozzle penetration into the bottles. Then, the grippers 115 are progressively lowered to allow the bottles to clear the nozzles 220 before the bottles reach the discharge wheel 125. As described further below, this penetration of the nozzle into the bottles enables sufficient dosage to be delivered to the interior of the entire bottle. While it is preferable to move the bottle relative to the emitter, in alternative embodiments the emitter may move relative to the bottle.

Each emitter 130 is activated by a power supply 225. The electrons emanating from the nozzle window 210 scatter in air, creating an electron beam energy plume that extends in 3 dimensions relative to surface of window. This energy plume sterilizes air and surfaces based on well known relationships between electron beam dose and microbiological reduction (such as published in Cleghorn et. al, "Sterilization of Plastic Containers Using Electron Beam Irradiation Directed through the Opening", Journal of Applied Microbiology, 2002). Electron scattering due to collisions of electrons with atmospheric molecules enables electron beam energy to reach surfaces that may be partially blocked due to the geometry of the surfaces.

Figure 1B:
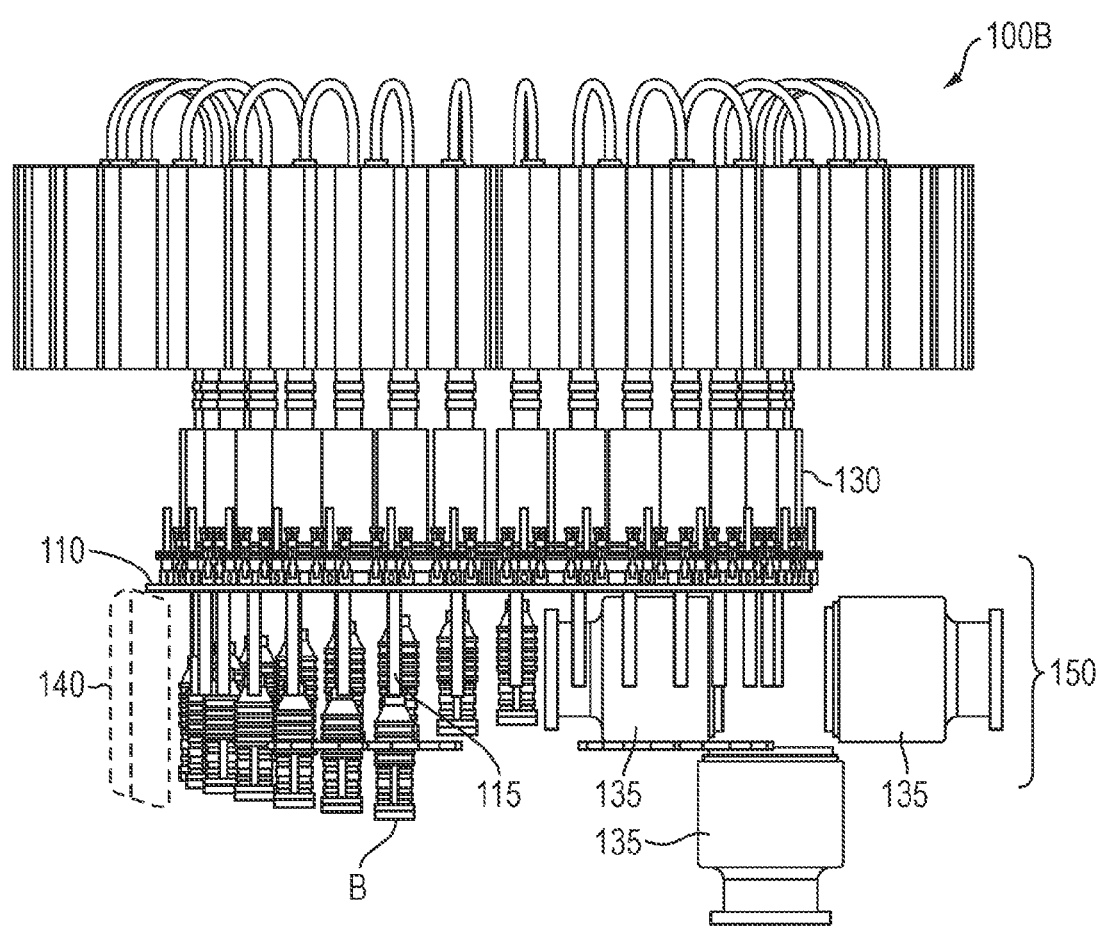
FIG. 1B is an alternative diagrammatic view of an exemplary electron beam sterilization apparatus in accordance with an illustrative embodiment of the present invention.

As shown in FIG. 1B, in order to sterilize the outside surfaces of the bottles B, one or more stationary electron beam emitters 135 may be positioned at fixed locations around the carousel 110. Illustratively, the external emitters 135 are arranged such that an external sterilizing dose may be achieved without rotating bottles B about their central axis. In alternative embodiments, the bottle grippers 115 may include provision for rotating the bottles to expose all sides of the bottles evenly to the electrons from the outside emitter(s) 135. As such, the description of external emitters arranged so that the bottles B do not need to be rotated about their central axis should be taken as exemplary only.

Alternatively, the sterile zone may be defined so as to only require the sterilization of upper portions of the bottle. In this case, the electron beam emanating from the nozzle may provide sufficient sterilization to upper portions of the bottle before and after the nozzle is inserted into the interior of the bottle. Thus, the number of external emitters may be reduced or avoided altogether. In this case, the relative movement of the nozzle with respect to the bottle would provide sufficient exposure time to effectively sterilize the relevant portions of the exterior of the bottle.

Figure 2B:
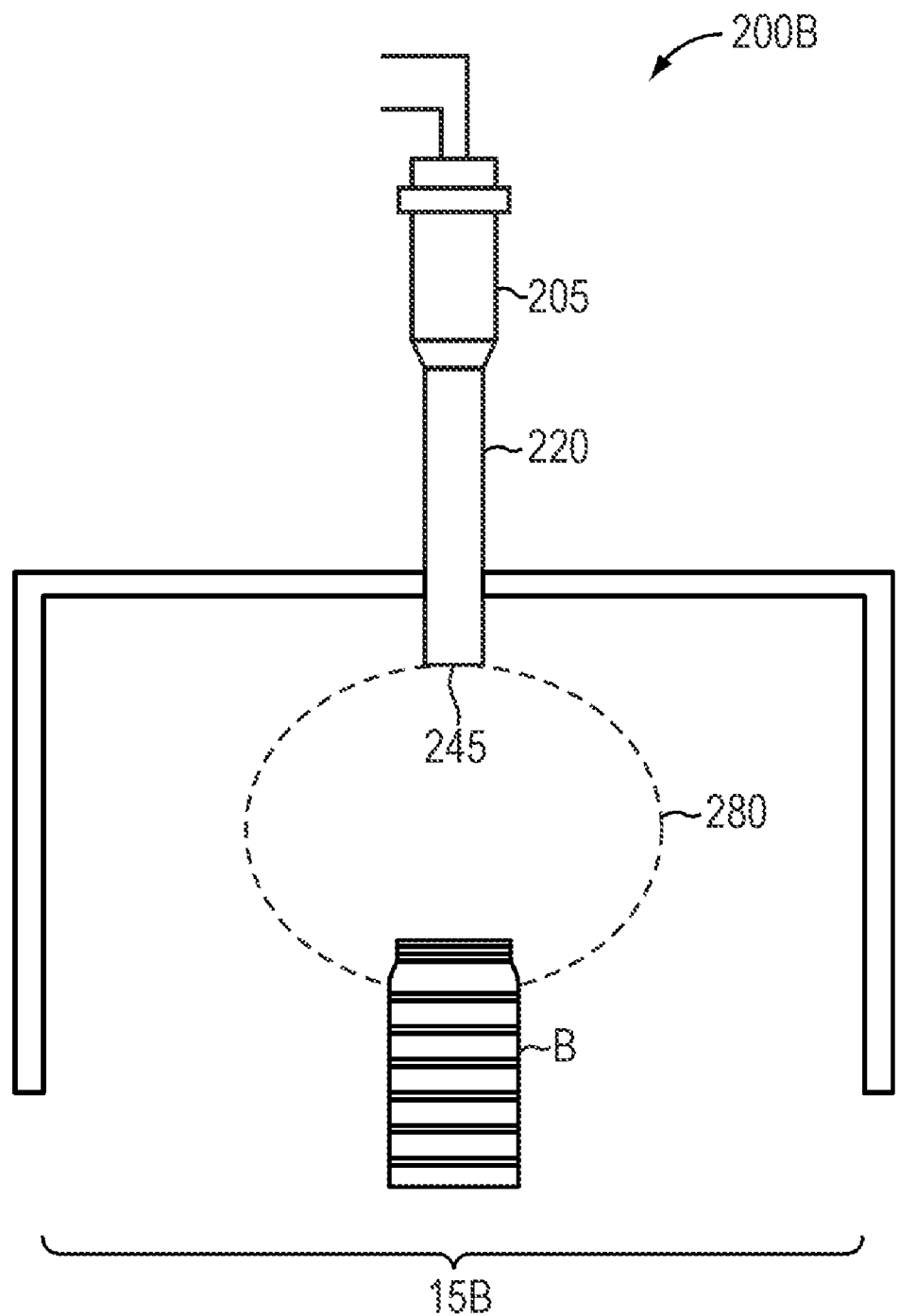
FIG. 2B is a side elevational view showing a portion of the exemplary electron beam sterilization apparatus sterilizing exterior surfaces of a bottle in accordance with an illustrative embodiment of the present invention.

FIG. 2B is a side elevational view showing a portion of the exemplary electron beam sterilization apparatus sterilizing exterior surfaces of a bottle in accordance with an illustrative embodiment of the present invention. Environment 200B shows that an electron beam plume 280 may be utilized to sterilize the exterior of a bottle B. The housing 205 and nozzle 220 enter into the sterile zone 15B and a plume 280 of electrons is generated from the electron beam window 245. The plume 280 is of sufficient diameter to sterilize the upper surface of bottle B as the nozzle 220 is inserted into the bottle. By controlling the speed at which the nozzle 220 is inserted into the bottle, an adequate dose to ensure sterilization can be achieved.

Figure 2C:
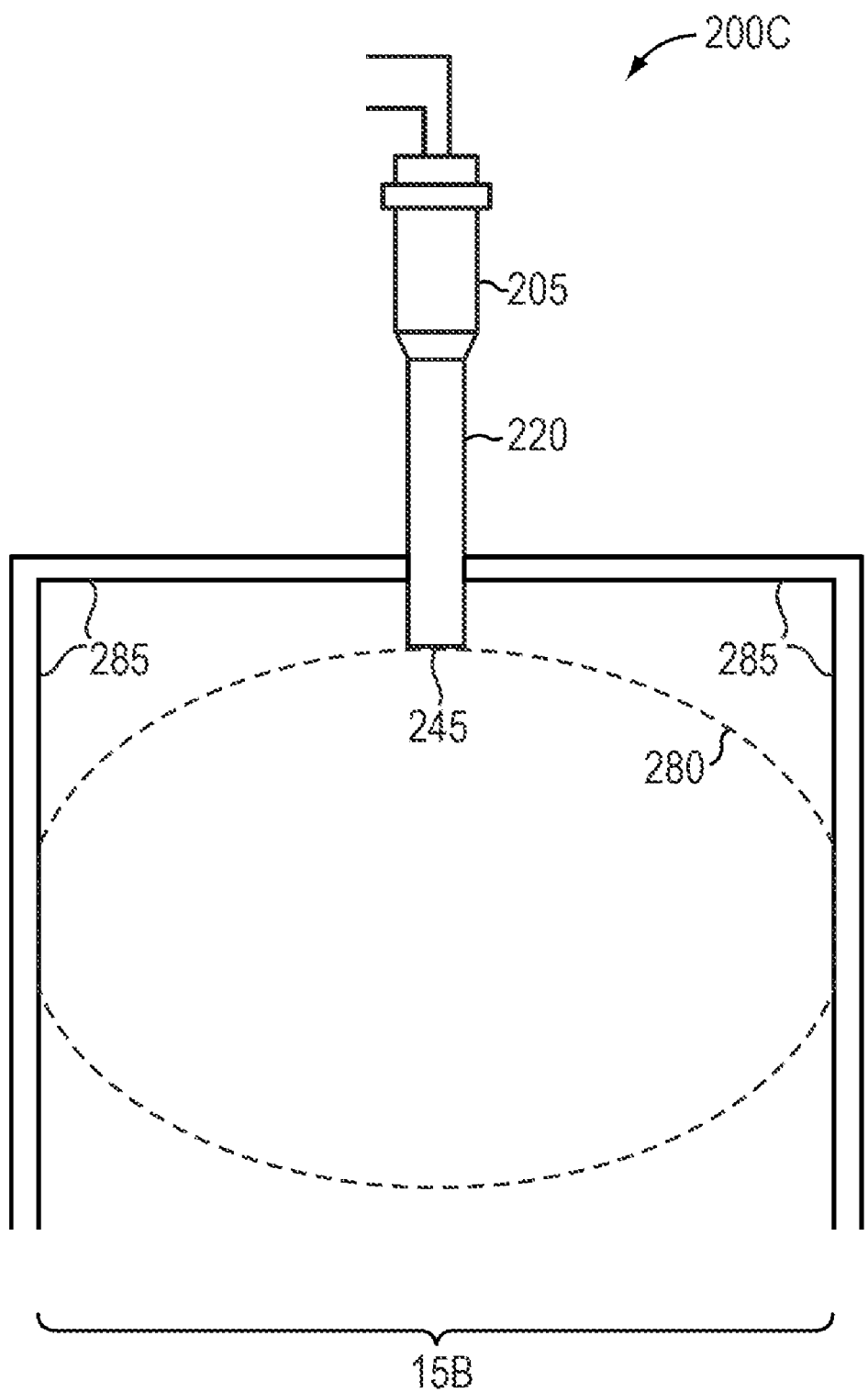
FIG. 2C is a side elevational view showing a portion of the exemplary electron beam sterilization apparatus sterilizing an interior of a chamber using a wider beam in accordance with an illustrative embodiment of the present invention.

FIG. 2C is a side elevational view showing a portion of the exemplary electron beam sterilization apparatus sterilizing an interior of a chamber using a wider beam in accordance with an illustrative embodiment of the present invention. Environment 200C illustrates that by utilizing sufficiently wide electron beam plumes 280, the interior walls 285 of sterile zone 15B can be sterilized.

The general operation of a bottle processing carousel such as carousel 110 is well known to those skilled in the art. Construction and operation of exemplary emitters 130, 135 is described, for example, in U.S. Pat. Nos. 5,962,995 and 6,624,229 and U.S. Publication No. 2008/0073549 A1, the contents of which are hereby incorporated by reference herein. An alternative approach to bottle sterilization would incorporate electron beam emitters position above the mouth of the bottles described in U.S. Pat. No. 6,221,216. Elements of bottle handling, shielding design and emitter control described herein may apply to this configuration as well. The overall apparatus may be controlled by a supervisory controller 605 described further below in reference to FIG. 6.

A clean process zone (or chamber) 150 where the bottles B are sterilized is illustratively defined by physical partitions 140 and positive internal gauge pressure may be provided to prevent ingress of contaminants into zone 150. Illustratively, the clean process zone 150 may be defined by physical partitions 140 and/or air pressure to provide an isolated environment where outside air is prevented from entering. Conventionally, the interior surfaces of chamber 150 as well as the nozzles 220 and other surfaces in the process chamber are cleaned in place (CIP) with various chemicals and them sterilized in place (SIP) using a chemical sterilant such as vaporized hydrogen peroxide (VHP) or peracetic acid (PAA) or by heat.

It is one important aspect of this invention that instead of using chemical sterilization or heat to sterilize the external surfaces of emitter nozzles 220 and the surfaces in the process chamber 150, during the SIP cycle, the present apparatus sterilizes such surfaces using electron beam radiation.

More particularly, in order to sterilize the surfaces in process chamber 150 as part of an SIP cycle, i.e. before the introduction of bottles, emitters 130 may be activated. The electron plumes from the nozzle windows 210 are free to contact the inside surfaces of housing 140 and other surfaces within chamber 150.

Figure 3:
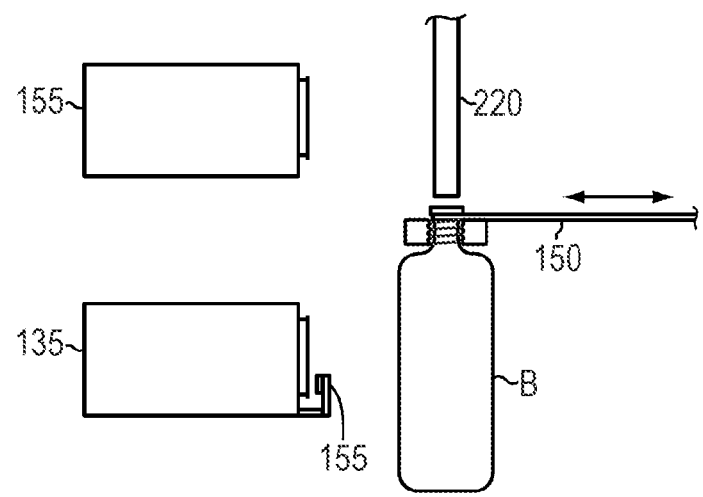
FIG. 3 is a similar view showing another part of the exemplary electron beam sterilization apparatus in detail in accordance with an illustrative embodiment of the present invention.

On the other hand, in order to sterilize the emitter nozzles 220 themselves, as shown in FIGS. 1B and 3, the emitters 135 provided for external bottle sterilization may be activated with bottles absent to sterilize the nozzles as they pass by.

Illustratively, the chamber 150 is configured so that chamber wall sterilization is accomplished using the same number and configuration of emitters 130, 135 used for container sterilization, although such operation may utilize different operating times and/or operating points, e.g., beam current and/or energy. If necessary to allow sterilization and/or decontamination of the process chamber surfaces, provision may be made for automatically displacing emitters 130, 135 before and/or during the chamber sterilization sequence. Alternatively, one or more additional emitters (not shown) may be provided and dedicated to process chamber sterilization.

Figure 6:
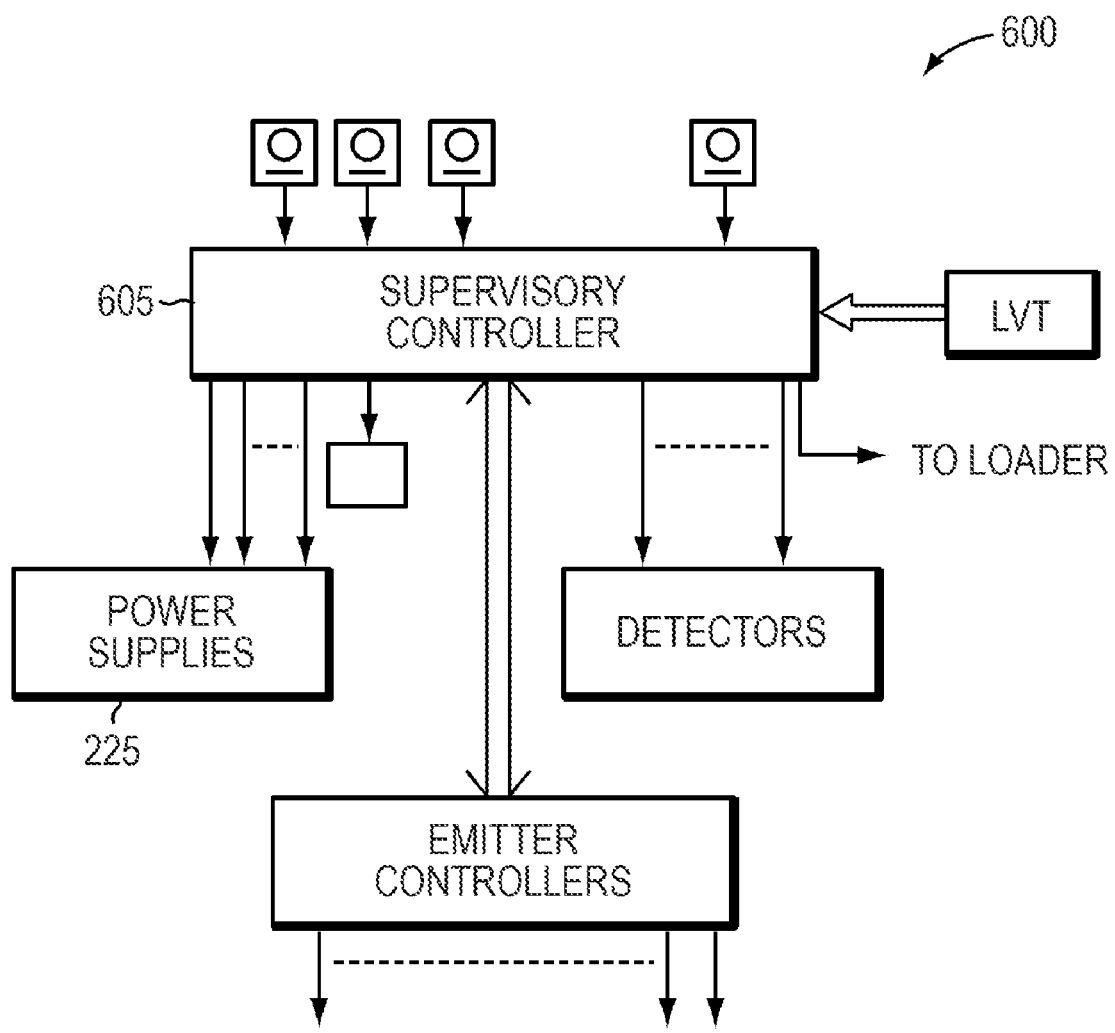
FIG. 6 is a block diagram showing the supervisory controller of the exemplary electron beam sterilization apparatus and relevant inputs to and outputs from that controller in accordance with an illustrative embodiment of the present invention.

In any event, such emitter and process chamber sterilization may be carried out simultaneously or sequentially under the control of controller 605, described below in reference to FIG. 6, and be optimized by proper selection of the emitter beam current and acceleration voltage of the emitters and/or by controlling the environment within chamber 150 during SIP, e.g. by providing a light gas or vacuum therein. Usually, the emitter operating parameters set by controller 605 are different during the SIP cycle than during the bottle sterilization cycle. For example during SIP, some emitters may operate at reduced power to avoid damage to the windows of other emitters. More generally, the SIP techniques described herein may be utilized to sterilize other ancillary equipment, i.e., non-nozzle and/or chamber walls, involved in a bottling operation.

During operation, the controlled sterile zone is defined as the boundary beyond which all machine surfaces and package surfaces interacting with the product to be packaged satisfy the requirements of sterility. This sterile zone is maintained with positive air pressure. It is necessary to ensure that once sterilized, the relevant packaging surfaces remain sufficiently sterile until they move into the controlled sterile zone. In order to ensure the interior of the bottle remains sufficiently sterile until passing into controlled sterile zone, the relative position of the electron beam emitter nozzle and bottle may be controlled so that after interior surfaces are complete, the electron beam plume may remain on the upper surface and finish of the bottle. The electron beam plume supplies sufficient energy such that any micro organism in the air that may otherwise transfer into the bottle interior through the mouth will be sterilized. The bottle will be removed from the electron beam plume within the controlled sterile zone, therefore preventing the possibility of recontamination of the relevant bottle surfaces before entering the controlled sterile zone. If necessary, exterior sterilization emitters may be positioned to sterilize the exterior surfaces and provide a transfer zone where bottles can be transferred from non-sterile zone to sterile zone without the risk of recontamination.

B. Dose Distribution

It is well known to those skilled in the art that the dose delivered to a surface is related to the current, the speed that the surface is moving and a constant. This relationship may be expressed as:

$$\text{Dose} = \frac{K_{(\varepsilon, V, d)} * \text{Current}}{\text{Speed}}$$

where K is a constant that depends on the emitter efficiency (ε), the accelerating voltage (V) and the window to surface distance (d).

When irradiating a three dimensional target such as a bottle B, the usual practice is to move the target at a fixed speed relative to an emitter 130, with the emitter operating at a fixed output energy and current. That is, in the exemplary FIG. 1 apparatus, the bottle grippers 115 are moved up and down at a fixed speed. In practice, this may result in some areas of the three dimensional target, i.e. bottle B, receiving excessive exposure to electrons which could cause adverse consequences, while other areas receive insufficient exposure to electrons so that those other areas are not sterilized adequately.

Figure 4:
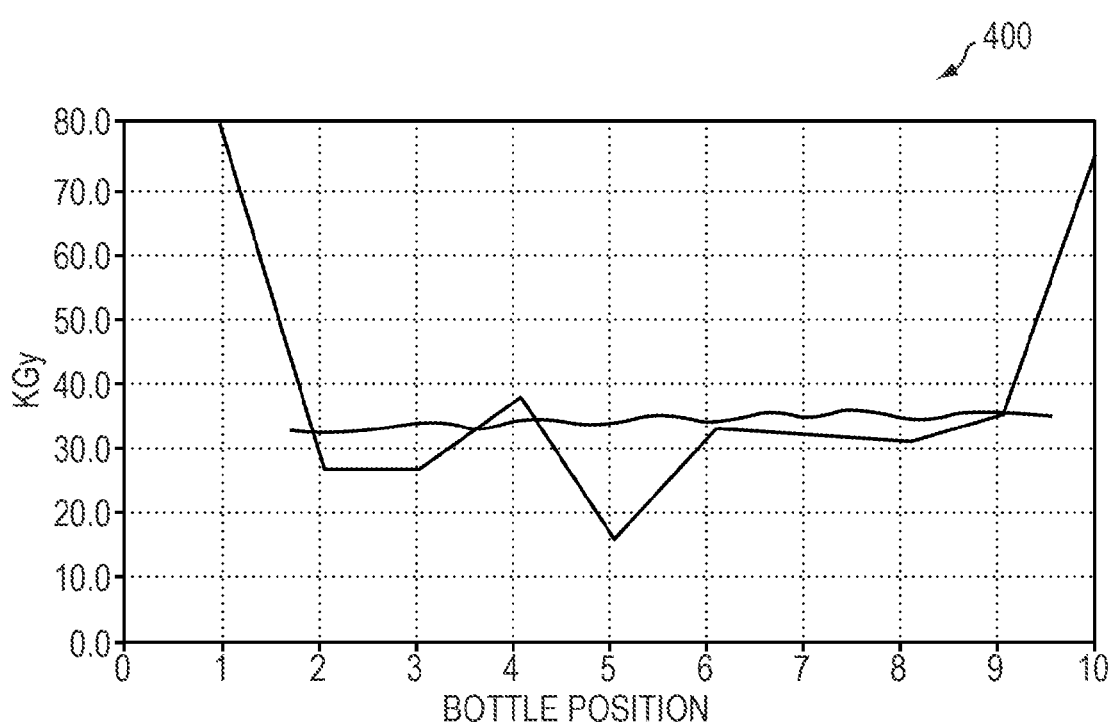
FIG. 4 is a graphical diagram comparing the sterilizing electron beam dose distribution for a typical bottle using a fixed electron beam emitter output and constant speed relative to the emitter with an idealized distribution for that bottle in accordance with an illustrative embodiment of the present invention.

For example, FIG. 4 shows the emitter dose distribution for a typical bottle B using a fixed output from an exemplary emitter 130 and a constant up/down movement of the bottle relative to the emitter in accordance with an illustrative embodiment of the present invention. In this example, a dose over 50 kGy is considered an excessive dose while a dose under 25 kGy is considered an insufficient dose. It should be noted that in alternative embodiments, the 25 and 50 kGy doses may vary and/or be substituted with differing values depending on the particular environment, material, etc. Waveform $P_1$ in FIG. 4 shows that there is a non-uniform dose distribution due to the three dimensional nature of bottle B. That is, when the bottle is at positions 1-2 and the window 245 of nozzle 220 is in the mouth and narrow neck of the bottle, the electron beam dose received is too great Likewise for bottle positions 9-10 when the window 245 is near the base of the bottle and the relative motion is being reversed. On the other hand, an insufficient electron beam dose is delivered to the surfaces at the sides of the bottle at position 5. Such variations in the applied electron beam dose adversely affect the applicability of electron beam sterilization for many such bottles and other irregular three dimensional targets.

Thus, in accordance with another aspect of this invention, controller 605 (FIG. 6) may be programmed to modulate the electron beam dose rate delivered by an emitter, e.g., emitter 130, 135, to a three dimensional target, e.g. bottle B. Such means may modulate the speed of the target relative to the emitter and/or modulate electron beam output from the emitter by altering emitter current and/or beam energy to change the dose rate to the target. The desired dose as a function of relative position of nozzle to bottle for a particular target geometry may be characterized in advance in stored in, e.g., a look up table (see FIG. 6). Illustratively, voltage and beam current are held constant in time while the relative speed of the container with respect to the stationary emitter is modulated. In this way, a substantially uniform dose distribution on the internal surface of the container may be achieved as represented by the idealized waveform $P_2$ in FIG. 4.

Such modulation may also be feedback-controlled by outputs from one or more sensors that produce a signal(s) related to the dose rate at the target and/or the relative positioning of the target.

For example, in case of the bottle shape represented by the waveform $P_1$ in FIG. 4, an excessive dose can be avoided by programming controller 605 to use a higher gripper 115 speed at bottle positions 1-2 when each nozzle 220 is in the mouth and neck of the associated bottle, e.g. higher by, say, a factor of 2-5 times the nominal speed. Also, when the neck is near the base of the bottle at positions 9-10, and the relative motion is being reversed, the output of the associated emitter may be modulated by reducing the beam output current and/or energy to create a dose rate that is lower by a factor of, e.g., 2-5 times the nominal dose rate. On the other hand, at bottle position 5, the gripper 115 may be slowed down and/or the dose rate increased. In any event, the objective is to obtain a substantially uniform dose distribution on all the interior surfaces of the bottle as represented by the idealized waveform $P_2$ in FIG. 4.

Thus, using the technique described herein, one can prevent both excessive and insufficient electron beam doses being applied to a three dimensional target, thereby greatly improving the overall speed and efficiency of such electron beam sterilization processes.

C. Electron Beam Output Measurements

Traditionally, electron beam output may be measured by monitoring feedback from the emitter power supply and the system controller. Using the known relationship of dose, speed, etc., a monitoring system can ensure sufficient dose to all surfaces.

In many applications, it may be desirable to measure the electron beam output from each emitter explicitly to confirm a reliable and repeatable electron beam dose at a target such as a bottle B. Traditionally, this has been done by periodic testing of the dose delivered by each emitter, for example by film dosimetry, and correlation to the power supplied to the emitter. This is both costly and time consuming and also means that any changes in beam output efficiency may not be discovered until the next periodic testing of the electron beam dose.

Thus, another important aspect of this invention is to supplement dosimetry by providing in situ sensors 155 as shown in FIGS. 1A and 3 which may monitor the beam outputs of emitters 130, 135 while the apparatus is in operation. The signal from each sensor 155 can then be used for a variety of different purposes. For example, the sensor output may be used simply to signal whether the associated emitter is on or off for maintenance purposes. sensor may also measure electron beam output with sufficient accuracy so readings can be compared to baseline readings taken at startup or installation in order to confirm electron beam emitter is operating with same efficiency. The dose-speed relationship may be used to calculate a measure efficiency (K) value to compare to baseline value in order to confirm emitter is operating at acceptable level of efficiency. If sensor identifies emitter is not operating properly (i.e. is off or is operating at an efficiency outside of acceptable levels), it may signal to the supervisory controller that the emitter has failed. The sensor may also be used in conjunction with a controller (e.g., controller 240 in FIG. 2) for feedback control to regulate the emitter output based on the sensed signal.

A sensor 155 may be fixed relative to each emitter at shown in FIG. 3 or, as seen in FIG. 1A, the two may move relatively so that the sensor 155 shown there can sense the output of multiple emitters 130 on the carousel as they pass by. In either event, this permits the output of each emitter to be measured during its operation, thereby ensuring that the target surface receives a proper sterilization dose. As noted above, such sensors also enable the monitoring of emitter performance for preventative maintenance purposes. In accordance with illustrative embodiments of the present invention, the sensors 155 may collect data to monitor the output of electron beam emitters, to determine the efficiency of emitters, to provide feedback control, etc. More generally, sensors 155 may be utilized to obtain data that may be utilized to provide feedback and/or diagnostic information to controller 605 in accordance with alternative embodiments of the present invention.

Figure 5:
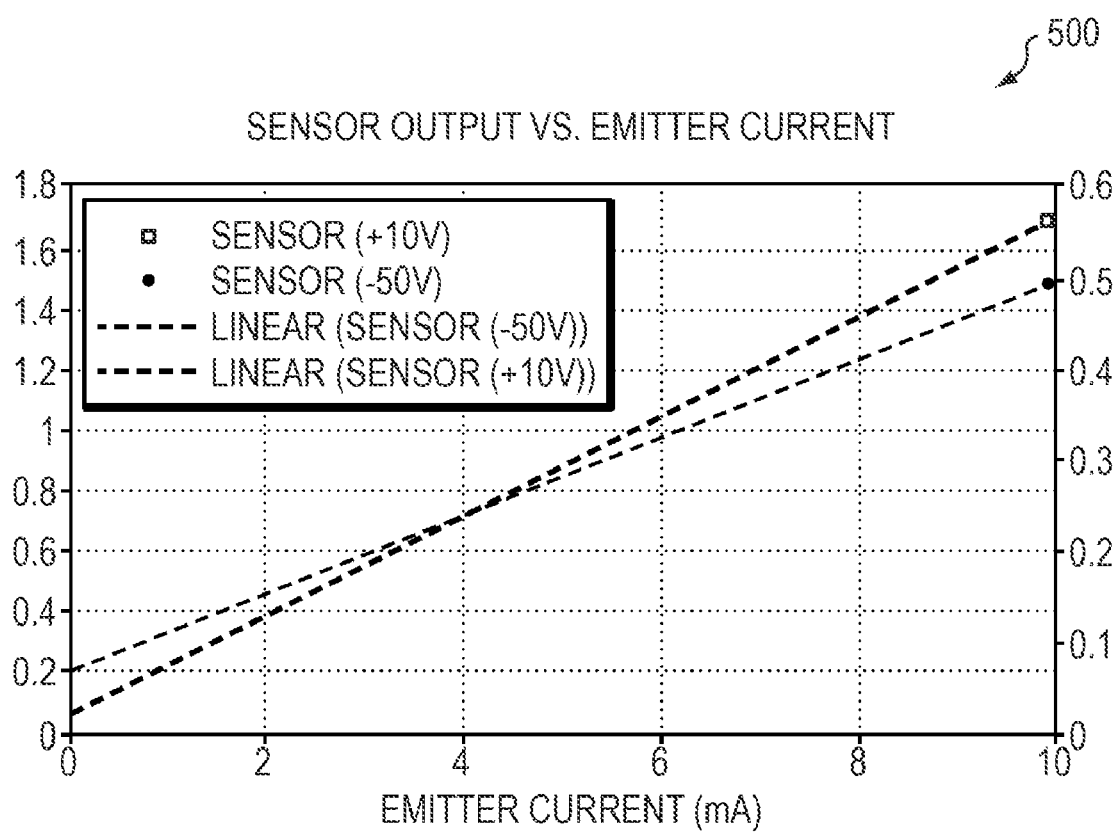
FIG. 5 is a graph showing electron beam sensor output as a function of emitter beam current in accordance with an illustrative embodiment of the present invention.

The sensor 155 may be electrical, thermal, x-ray, visible light detection or other type of sensor. Electron beam sensing using calorimetry is also feasible. An illustrative suitable electron beam sensor is described in U.S. Pat. No. 6,919,570, the contents of which are hereby incorporated by reference herein. Alternative sensors may include a negatively biased probe that is directly exposed to the electron beam in the atmosphere. The electron beam will create secondary electrons emitted from the probe and which are accelerated away from the probe by the negative bias. The measured probe current thus becomes a measure of the beam output. The sensor 155 may also measure the beam current drawn to a sensor probe from atmospheric plasma when the probe has a positive bias. FIG. 5 is a plot of the sensor output as a function of ebeam current for those two types of sensors in accordance with an illustrative embodiment of the present invention. As seen there, the sensor output signal is substantially proportional to the electron beam current.

D. Fault Tolerance

In an electron beam sterilization apparatus of this general type, a failure of an emitter 130, 135 or of its power supply 225 will reduce the sterilizing dose of ionizing radiation from that emitter. An emitter failure often involves a breach of the emitter vacuum chamber 210 (FIG. 2), causing a short circuit. This requires that the emitter's power supply 225 be shut off and that the emitter be disconnected from the system or replaced, resulting in potential downtime and lost productivity. If a single power supply serves several emitters, the problem is compounded.

Also, an electron beam emitter, like typical high voltage devices, suffers occasional arcing. During an arc, the beam output is disrupted and with it the sterilizing dose of ionizing radiation to the target, e.g. bottle B. Resultantly, some of the bottles B being processed may not be sterilized adequately.

Thus, it is an additional feature of this invention that provision is made for monitoring emitter failure and the occasion and duration of emitter arcing to determine whether or not a proper sterilization electron beam dose has been applied by that emitter to a particular bottle.

For this, the supervisory controller 605 (FIG. 6) may keep track of the position of all the bottles entering the overall conveyor system and, using the data from the LUT, may calculate the proper beam set point for each emitter.

The desired dose range can be loaded into the controller 605 at the beginning of each run and the value of the current measured in real time using known means. If the current value falls outside the allowable band, the controller may initiate the actions described below.

In response to an emitter failure, the controller 605 may perform recovery operations depending on the type of failure detected. If a hard, i.e., non-arc, failure is detected that will require replacement/off-line repair of an emitter, the controller 605 may send instructions to the loader in FIG. 1A to not load bottles to the station of the infeed wheel 105, that corresponds to the carousel 110 position containing a defective emitter 130. For example, in a thirty-head emitter carousel 110, if one emitter 130 fails, the controller 605 may leave one open position for every twenty nine bottles introduced into the conveyance line by the loader. This ensures that the failed emitter is "skipped" thereby ensuring that bottles are not improperly sterilized.

Should the controller determine that particular bottles have not been properly sterilized due to an electron beam emitter failure, the controller 605 will track the bottles B served by the defective emitter 130 and eject them from the line after they leave the carousel 110, say, by activating a stationary linear actuator (not shown) positioned under the transfer wheel 125 in FIG. 1 causing the actuator to "kick" the potentially improperly sterilized bottles B from the line. Alternatively, the actuator may mark the improperly sterilized bottles as "defective" and hence subject to rejection down the line. Alternatively, the gripper may "drop" the affected bottle while on the sterilization carousel to a rejection system (not shown) below.

Should an arc event be detected, i.e., the defective emitter is producing at least some beam output, the controller 605 may analyze whether the bottle will accumulate sufficient dose on all surfaces in order to be classified as sterile. It may be preferable to set the target minimum dose to some level above the required minimum dose in order to compensate for occasional arc events. If the controller determined that insufficient dose is delivered due to an arc event, it may modify the power to that emitter and/or the vertical stroke of the associated gripper 110 so that the bottle B does receive the proper electron beam does, e.g., if an arc occurs, the rest of stroke cycle may be slowed down to compensate. Alternatively, the controller 605 may initiate proper control operations to the carousel and defective emitter so that the associated bottle receives the reduced electron beam doses at one or more successive steps or increments of the carousel until the reduced doses total the correct amount. For example, the controller 605 may slow the line speed down to allow an emitter operating at reduced power additional time to complete sterilization of a bottles.

In the case of the external emitter(s) 135, extra emitters may be utilized to provide such dose redundancy. Thus, if one emitter, say, emitter 130, fails, the controller 240 may switch out the emitter and activate its mate. Preferably, during normal operation of the apparatus, the two emitters (primary and secondary) are both operated at half power. Then, if one emitter fails, the controller 240 may automatically double the power to the other so that the bottles B targeted by that emitter pair receive a normal electron beam dose.

E. Emitter Identification and Compensation

In a multi-emitter system, such as the FIG. 1 apparatus, shown above in FIGS. 1A, B, it may be desirable to regulate the electron beam levels, energy or current i, to compensate for differences in efficiency and provide consistent dose, across all the emitters. For this, a novel apparatus in accordance with an illustrative embodiment may include an emitter control system which can automatically adjust the emitter set points when the emitters are replaced, all with little or no operator intervention and with limited down time.

Accordingly, it is a further aspect of this invention to provide an automatic emitter identification and compensation arrangement which can improve the up-time of a multi-emitter system such as the exemplary apparatus in FIGS. 1A, B. For this, an ID tag 230 such as a bar code, RFID tag, printed label, marking or the like may be provided on each emitter 130, 135 as shown in FIG. 2. Preferably, the ID tag carries readable data reflecting certain emitter characteristics including emitter efficiency. Also, as shown in FIG. 2 the apparatus may include an appropriate ID tag reader 235 capable of reading any data on the particular ID tag 230 as the associated emitter moves by, or is opposite, the reader.

Preferably, each emitter 130, 135 has a dedicated emitter controller 240 associated with that emitter's power supply 225 as shown in FIG. 2. All of the emitter controllers 240 are, in turn, be controlled by the supervisor controller 605 (FIG. 6) which is responsible for the overall operation of the apparatus, including that of the emitters.

Generally, there are two types of reading systems, namely "centralized" and "distributed". In a centralized system, the supervisory controller 605 receives data from each ID tag reader 235 and provides each emitter with a modified set point based on the stated efficiency of each emitter.

On the other hand, in a distributed system, each emitter controller 240 should include a reader 235 capable of reading data from the associated emitter label. Then each emitter controller 240 can modify the power supply 225 for that emitter based on the actual emitter efficiency, the nominal set point being provided by the supervisory controller 605. Alternatively, a serial numbering device may be attached to each emitter and connected by a dedicated cable to that emitter's controller 240. As another option, communication to a serial memory may be "piggy-backed" on an existing electrical connection, for example, via modulation of a carrier frequency.

In general, non-contact reading systems such as bar codes, RFID tags, etc. are more appropriate for centralized readers whereas wired systems are, by definition, more suitable for distributed readers.

In either event, when the emitter characteristics are stored on an ID tag attached to an emitter, the efficiency of the emitter is available directly. On the other hand, when only an emitter ID is on the tag with the emitter, that ID may be used to retrieve emitter characteristics and efficiency from a database provided by the manufacturer.

Instead of storing efficiency and other data as a bar code on an emitter 130, that data may be retained in a separate dedicated data storage device such as removable flash memory 250 which is paired with the corresponding emitter controller 240 as shown in FIG. 2. When the memory 250 is plugged into emitter controller 240, that controller controls that emitter's power supply 225 to take into account that efficiency of the emitter 130.

As indicated above, when irradiating a target with an electron beam in a continuous flow application, it may be necessary to indicate when an insufficient electron beam dose has occurred due to arcing in an emitter such as emitter 130, 135. In the exemplary FIG. 1 apparatus, the supervisory controller 605 should be able to monitor the output of all of the emitters for arcs to determine which emitters have delivered a sufficient dose over any period of time. To do that, each emitter must be monitored, either by direct measurement or by continuous network communication with a sufficient resolution or bandwidth to detect even brief arc events.

The bandwidth required to monitor multiple emitters increases as the number of emitters increases and as the duration of the arcing decreases. In a multiple emitter system, less bandwidth is required if each emitter includes a mechanism to monitor its own arc activity to determine if that emitter has delivered a sufficient dose to its target and thereafter report the result to the supervisory controller 605.

Accordingly, it is an additional object of this invention to install the necessary hardware and software in the supervisory controller 605 to:

1. control each individual emitter controller 240;
2. indicate to each emitter controller 240 when a new target, i.e. bottle B, has been loaded at the associated emitter location. This may be a signal from controller 605 that controls the carousel 110 and coordinates all the emitter controllers 240. The signal may be initiated by an optical, capacitive, magnetic, inductive, proximity, etc. sensor such as the sensor 255 shown in FIG. 2;
3. optionally provide a signal to each emitter controller 240 when the target is to be unloaded from the particular emitter location;
4. monitor the aforesaid signals to establish the time during which the material is to be exposed;
5. count the number of arcs detected by each emitter controller, or accumulate the total time that radiation is absent due to arcs for each exposure cycle;
6. compare the result of the aforesaid count to a pre-defined or programmable limit to establish if the bottle material has received a sufficient dose;
7. provide a signal, by a discrete electrical connection or via a network connected to each emitter controller, to the customer indicating if the bottle material did or did not receive a sufficient exposure;
8. control the previous signal such that the result of the exposure cycle is indicated either:
   i. after the exposure cycle,
   ii. at the earliest point during the exposure cycle when it has been established by (6) that a minimum exposure level has been reached,
   iii. at the earliest point during the exposure cycle when it has been established by (6) that a maximum number of arcs (or duration of radiation loss) has been reached, and
9. minimize the communication bandwidth requirement between a supervisory controller and all emitter controllers by indicating only the result of the exposure cycle (pass or fail) once per exposure cycle.

In the counting of arcs in the aforesaid paragraph 5, the arc count may be stored locally in the emitter controller 240 for each emitter. That controller may carry out a continuous dose calculation for that emitter and issue a pass or fail signal to the supervisory controller 605, or send back a dose value to that controller. To detect the arcs, the beam current and/or voltage may be monitored. Alternatively, beam output may be detected by a sensor such as sensor 155 in FIGS. 1A and 3 may be associated with each emitter 130, 135. The emitters controllers 240 may keep track of the dose values locally and control the corresponding power supplies 225 to raise or lower the electron beam doses from the corresponding emitters accordingly or send pass/fail signals to the supervisory controller 605. In either event, the power to the corresponding emitters may be modified and/or the bottle up/down stroke may be changed to compensate.

Since certain changes may be made in carrying out the above methods and in the constructions set forth, it is intended that all matter contained in the above description or shown in the accompanying drawings shall be interpreted as illustrative and not in a limiting sense. It should be noted that controller 605 may be implemented as an industrial grade controller including, e.g., a PLC, etc. Further, it should be noted that various control processes described herein may be implemented in software executing on a processor, hardware, firmware and/or a combination thereof.

F. Shielding Arrangements

In illustrative embodiments of the present invention, a sterilization carousel, described above in reference to FIGS. 1A and 1B, is utilized with one or more feed mechanisms to enable bottles (or other packaging) to be transported onto and discharged from the sterilization carousel. In accordance with alternative embodiments of the present invention, the sterilization carousel and feed mechanisms are shielded in order to minimize the amount of radiation that escapes from the shielded region. Illustratively, the shielding is configured such that an x-ray must reflect at least three times before reaching an unshielded region. Exemplary electron x-ray radiation paths are discussed below in reference to FIGS. 23-26. FIGS. 7-22, described further below, illustrate various alternative embodiments for configuring a sterilization carousel and input/discharged feed mechanisms in accordance with various alternative embodiments of the present invention. The various embodiments shown and described work to reduce the amount of shielding required, and thereby lower cost, while maintaining adequate safety for humans in the vicinity of a sterilization carousel during operation.

Figure 7:
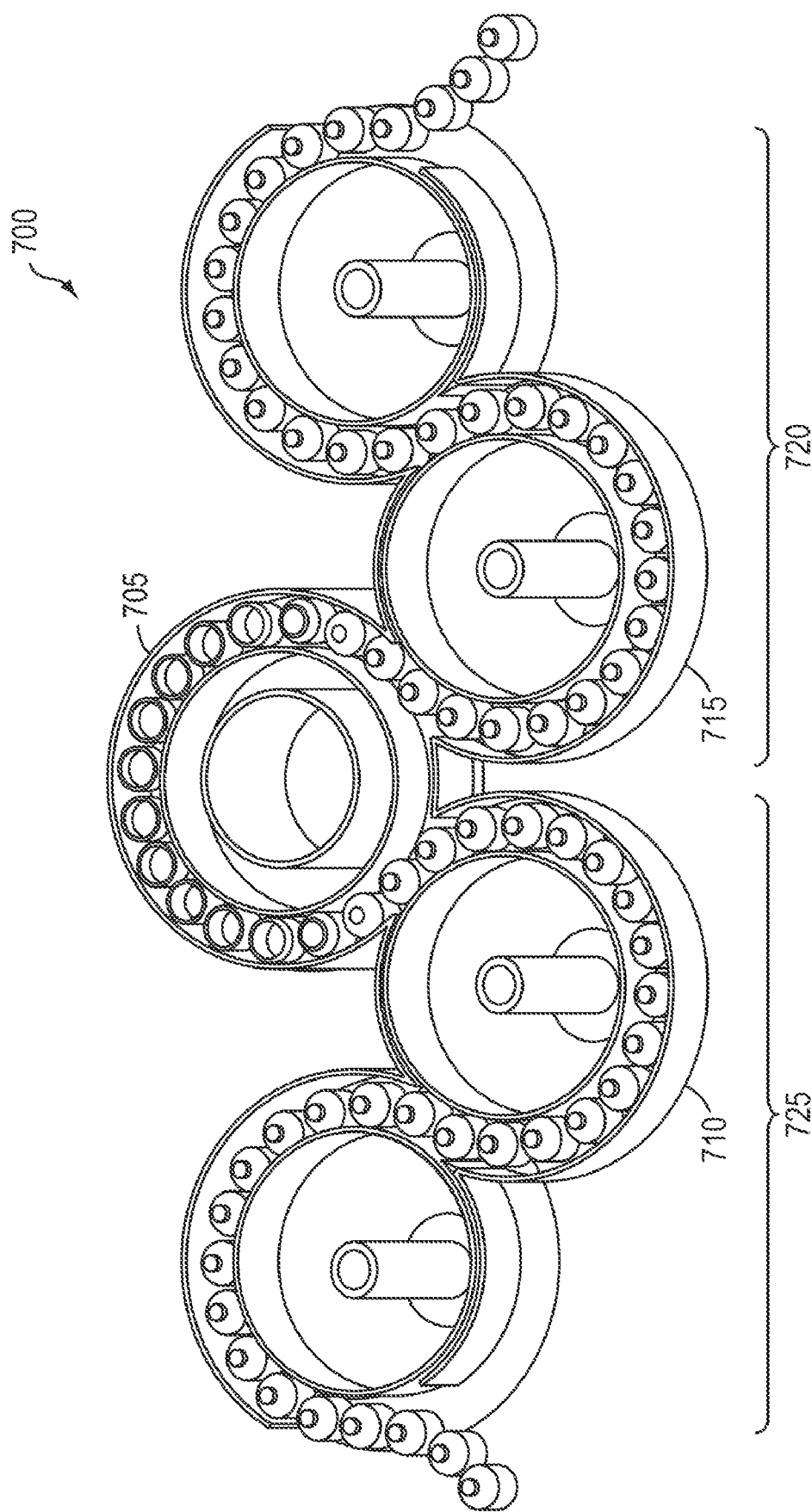
FIG. 7 is a top cutaway view of an exemplary enclosed electron beam labyrinth sterilization carousel environment in accordance with an illustrative embodiment of the present invention.

FIG. 7 is a top cutaway view of an exemplary enclosed electron beam labyrinth sterilization carousel environment 700 in accordance with an illustrative embodiment of the present invention. An input carousel 710 feeds bottles onto the sterilization carousel 705. Input carousel 710 may accept bottles from additional carousels (not shown) as they move along a production line environment. Illustratively, the input carousel 710 may be operatively interconnected with a linear feed mechanism to enable the installation of a sterilization carousel 705 and input carousel 710 in a linear feeding production environment. As such, it should be noted that input feed carousel 710 may accept bottles from any type of the bottle transport mechanism in alternative embodiments of the present invention. Sterilized bottles are then discharged onto discharge carousel 715. The discharged carousel 715 may also be operatively interconnected with additional carousels (not shown) configured to move sterilized bottles for later steps in processing, for example filling with a liquid. Similarly to that described above in reference to carousel 710, output carousel 715 may also be operatively interconnected with alternative feed mechanisms including, for example, a linear feed mechanism. As such, the illustrative embodiment shown in FIG. 7 should be taken as exemplary only.

Illustratively, region 725 comprises a non-sterile zone. A sterile boundary exists at some point in the sterilization carousel, or directly after the carousel, which defines an aseptic zone 720 in which the bottles as well as all machinery surfaces and air are considered sterile. That is, before the bottles reach the sterile boundary, they are considered to be non-sterile. Once the bottles have been sterilized, they are discharged onto discharge carousel 715 and are considered to be aseptic and ready for filling with a suitable liquid.

Figure 8:
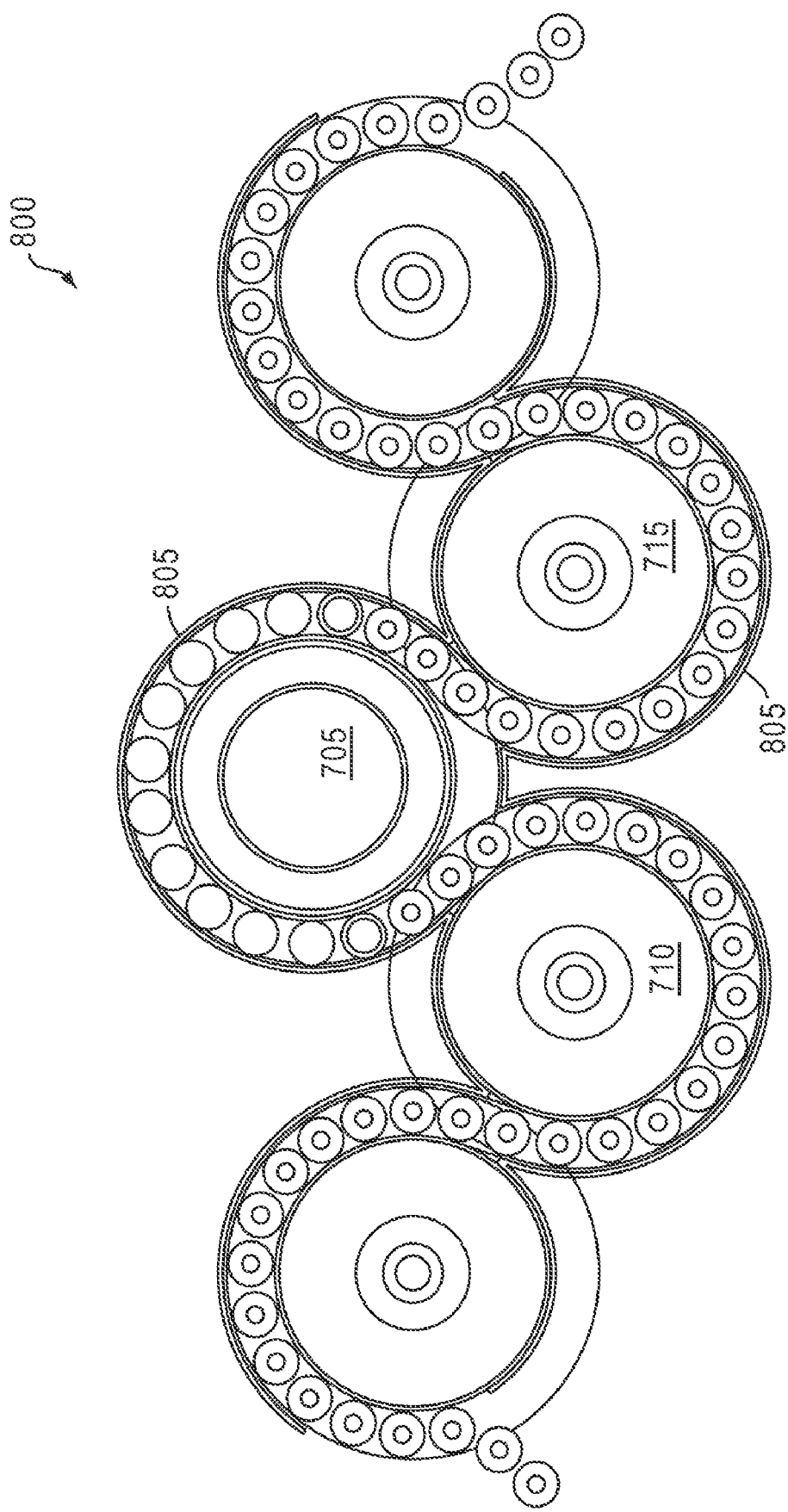
FIG. 8 is a schematic diagram of an exemplary enclosed electron beam labyrinth sterilization environment in accordance with an illustrative embodiment of the present invention.

FIG. 8 is a schematic diagram of an exemplary enclosed electron beam labyrinth sterilization environment 800 in accordance with an illustrative embodiment of the present invention. Illustratively, the labyrinth environment is the same as that shown above in reference to FIG. 7. A sterilization carousel 705 accepts bottles from the input carousel 710 and discharges them to discharge carousel 715. The carousel environment 800 is shielded to prevent x-ray radiation from reaching exterior to the shielded environment without requiring a minimum of three reflections. Illustratively, shielding is placed along lines 805 on the sterilization carousel 705 and the input and discharge carousels 710, 715. Illustratively, the shielding comprises lead sandwiched between two layers of stainless steel. However, it should be noted that in alternative embodiments the composition of the shielding may vary. As such, the description of a layer of lead between layers of stainless steel should be taken as exemplary only. It should be expressly noted that in alternative embodiments additional and/or differing materials may be utilized for the shielding for use in various embodiments of the present invention. Furthermore, the relative thicknesses of the layers may vary depending on the strength of the electron beam emitter is being utilized. As will be appreciated by one skilled in the art, the more energy that an electron beam emitter produces requires thicker shielding to prevent x-ray radiation from escaping through the shielding materials. In an illustrative embodiment, for electron beam emitters that utilize 150 kV, a typical shielding would comprise approximately 7 millimeters of lead. Typically the lead is clad on either side with stainless steel approximately 30-60 thousands of an inch thick. Alternate shielding mechanisms could be used, e.g., approximately 90 mm of stainless steel with no lead. However, it should be noted that these values are illustrative only and that differing values they be utilized in accordance with alternative embodiments of the present invention.

Figure 9:
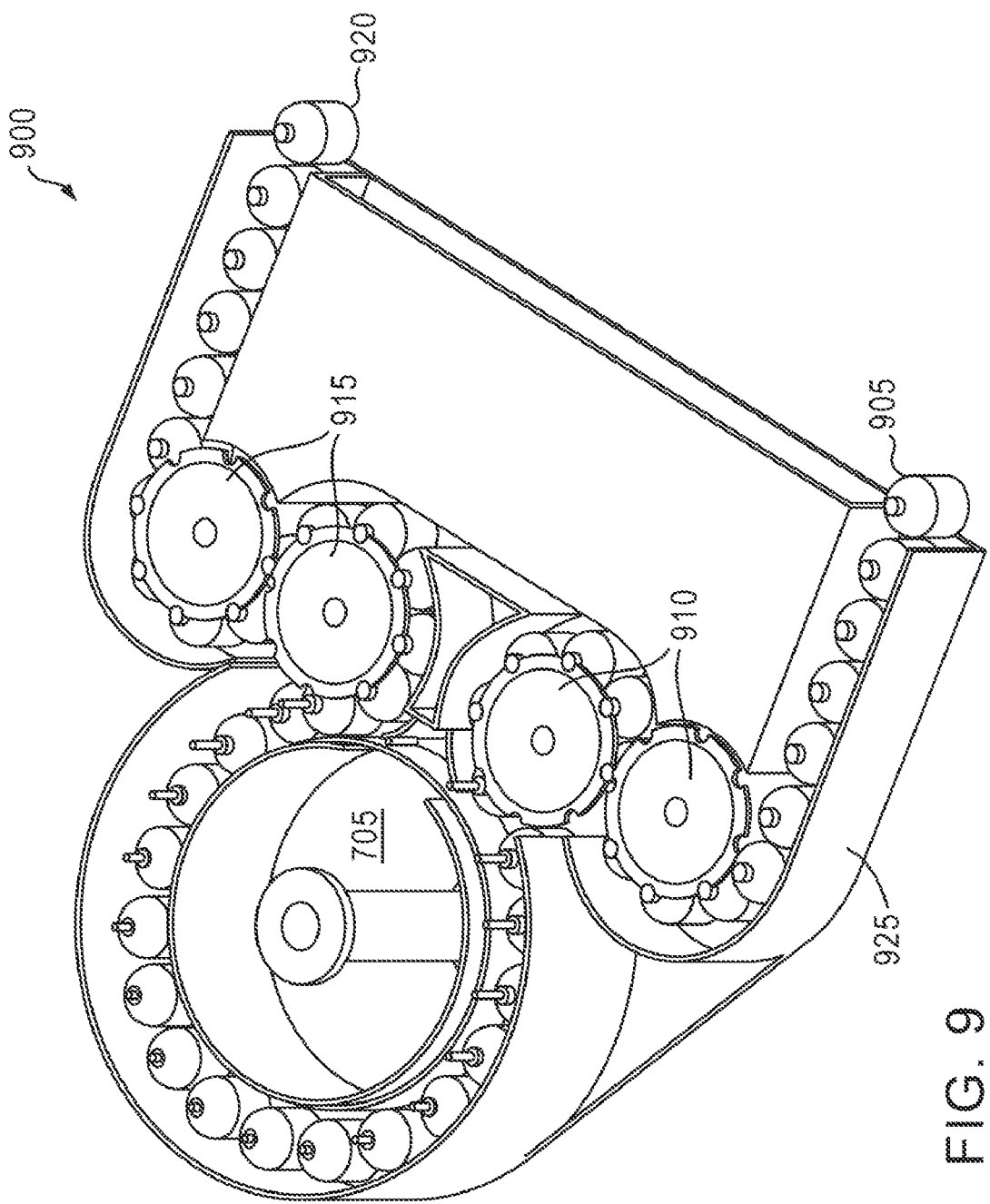
FIG. 9 is a top view of an exemplary enclosed electron beam labyrinth sterilization environment with linear input and discharge feeds in accordance with an illustrative embodiment of the present invention.

FIG. 9 is an exemplary top view of an enclosed electron beam labyrinth sterilization environment 900 with linear input and discharge feeds in accordance with an illustrative embodiment of the present invention. An exemplary sterilization carousel 905 is operatively connected with a series of input carousels 910 that are then connected to a linear input feed 905. Similarly, one or more discharge carousels 915 are operatively connected to a linear discharge feed 920. In operation, bottles may enter environment 900 via linear input feed 905 and be accepted into the input feed carousels 910 before being transferred to the sterilization carousel 705. Once sterilized, bottles are fed to discharge carousels 915 before being transferred to the linear discharge feed 920. Illustratively, the linear feeds 905-920 may utilize a chain transport mechanism as is well known in the art. In alternative embodiments additional and/or differing a linear transport mechanisms may be utilized. Illustratively, the input and discharge carousels 910, 915 are of a smaller diameter than the sterilization carousel 705. However, in alternative embodiments the various sizes may differ. As such, it should be noted that the representation of the input and discharge carousels having a smaller size than the sterilization carousel should be taken as an exemplary only. The environment 900 illustrated in FIG. 9 may be utilized to implement a sterilization carousel in production environments that utilize linear feed mechanisms. By utilizing a plurality of input and discharge carousels 910, 915, the region to be shielded may be reduced, thereby saving expenses in material for shielding.

Figure 10:
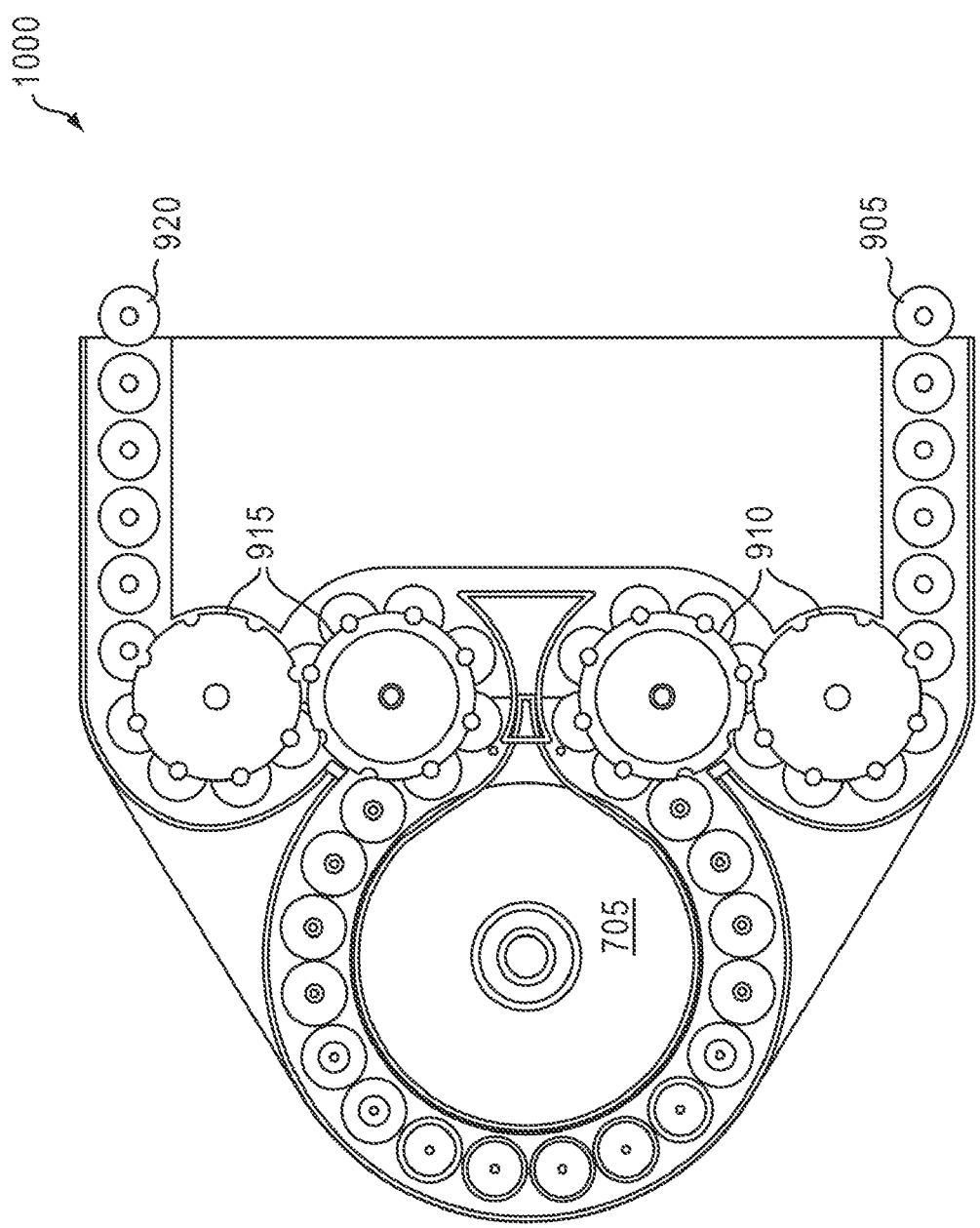
FIG. 10 is a schematic diagram of an exemplary enclosed electron beam labyrinth sterilization environment with linear input and discharge feeds in accordance with an illustrative embodiment of the present invention.

FIG. 10 is a schematic diagram of an exemplary enclosed electron beam labyrinth sterilization environment 1000 utilizing linear input and discharge feeds in accordance with an illustrative embodiment of the present invention. Environment 1000 represents a similar environment to that shown above in reference to FIG. 9. A sterilization carousel 705 excepts bottles from a plurality of input carousels 910 and discharges sterilized bottles onto discharged carousels 915. A linear input feed 905 of bottles feed to input carousels 910. Similarly, a linear discharge feed 920 accepts bottles from discharge carousels 915. The shaded region represents the area of the sterilization carousel and input/discharge carousels that would be shielded in accordance with an illustrative embodiment of the present invention. By reducing the size of the region to be shielded, there is a concomitant savings in the cost of shielding. Furthermore, the exemplary environments 900, 1000 illustrate techniques for enabling a sterilization carousel to be utilized with linear feed production environments. That is, a sterilization carousel may be easily integrated into a pre-existing system or environment that utilizes linear feed mechanisms.

Figure 11:
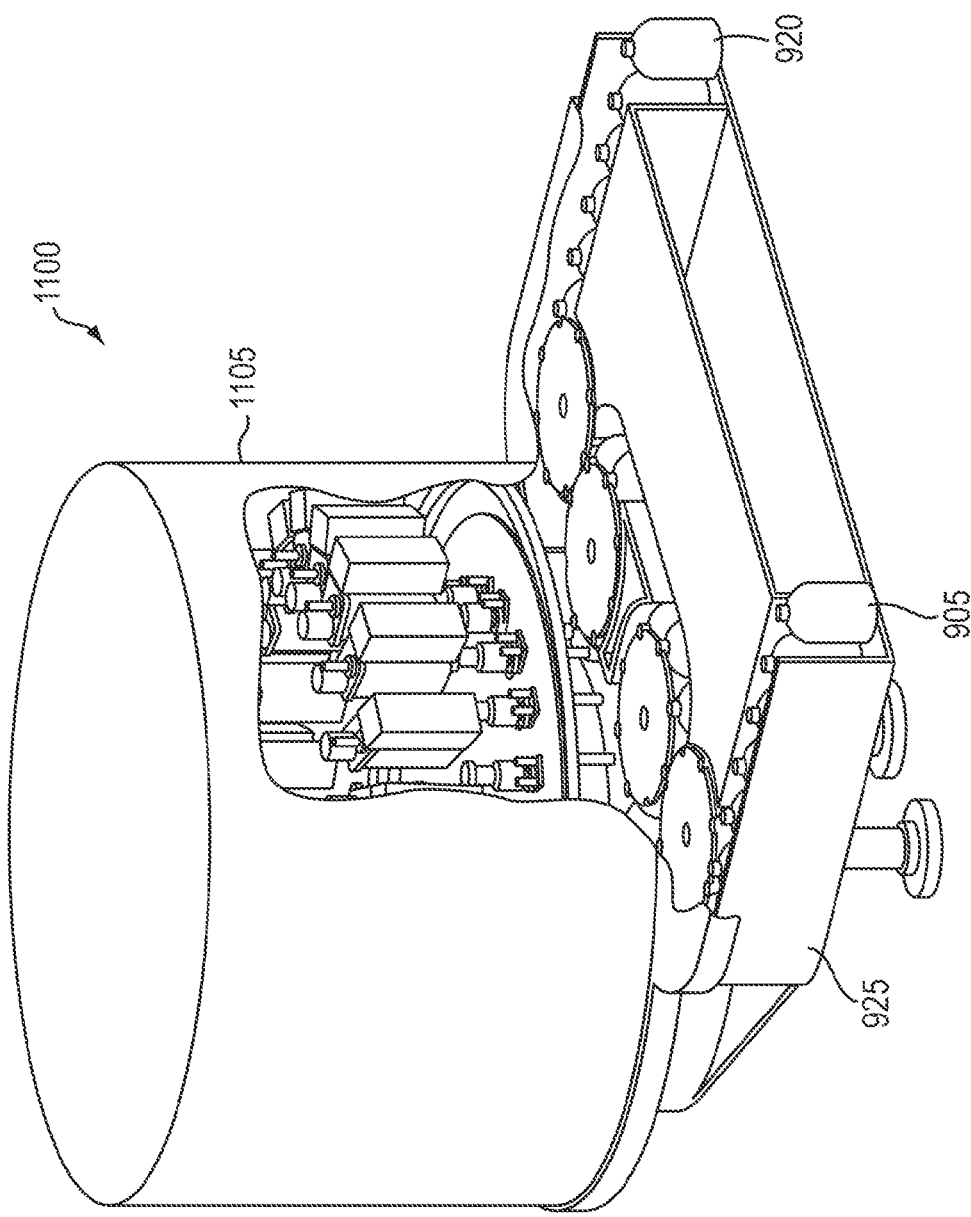
FIG. 11 is a partial cutaway view of an exemplary enclosed electron beam labyrinth sterilization environment with linear input and discharge feeds showing a removable shield for electron beam power supplies and emitters in accordance with an illustrative embodiment of the present invention.

FIG. 11 is a partial cutaway view of an exemplary enclosed electron beam labyrinth sterilization environment 1100 having linear input and discharge feeds illustrating a removable shield in accordance with an illustrative embodiment of the present invention. Illustratively, the electron beam power supplies and emitters are covered by shielding 1105. In an illustrative embodiment of the present invention, shielding 1105 may be removable to enable access to the electron beam power supplies and/or emitters for repair and/or maintenance. In alternative embodiments of the present invention, a maintenance access hatch (not shown) may be integrated into the shielding 1105. The hatch, which may be any radiation tight hatch, may be opened to enable access to one or more of the power supplies and/or emitters.

Figure 12:
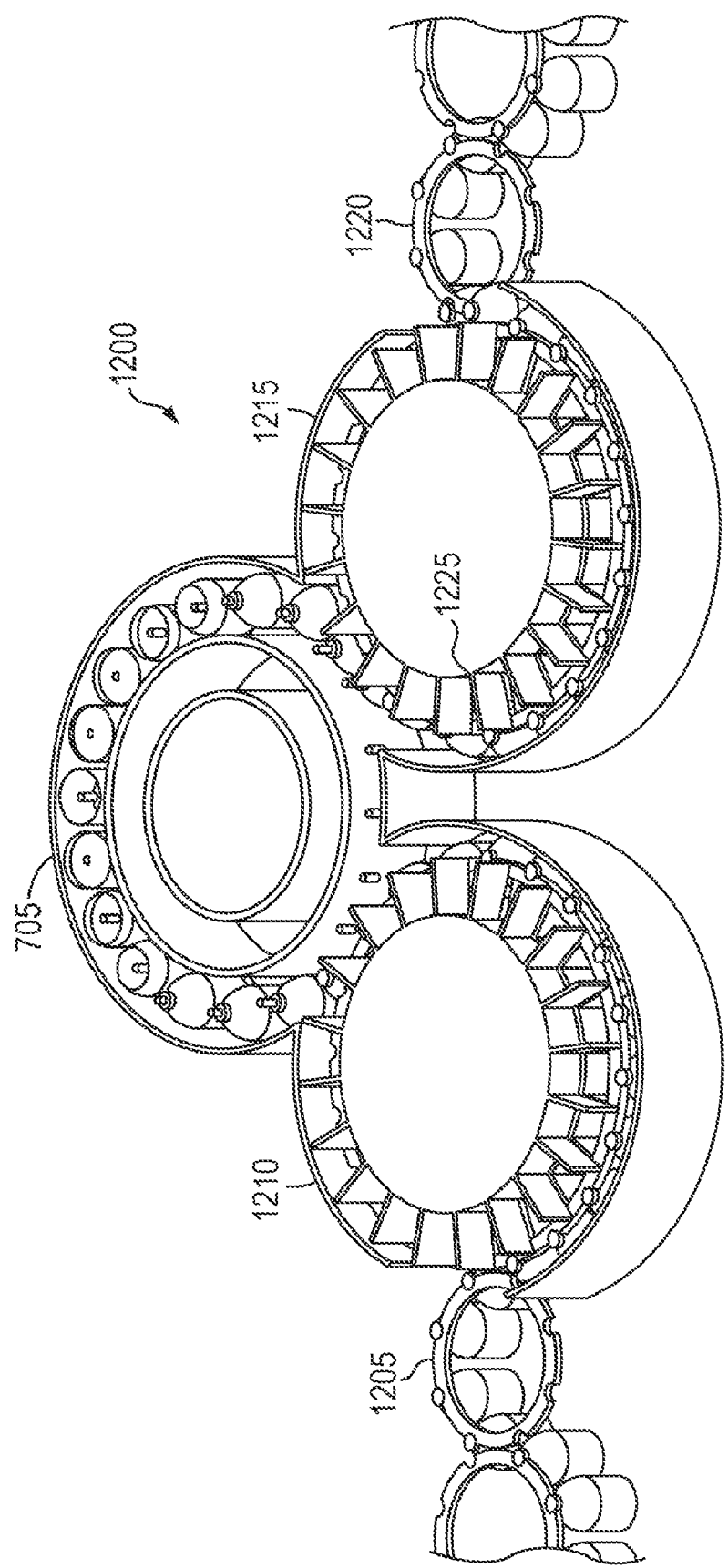
FIG. 12 is a top view of an exemplary enclosed electron beam sterilization labyrinth environment utilizing carousel-based baffles in accordance with an illustrative embodiment of the present invention.

FIG. 12 is a top view of an exemplary enclosed electron beam sterilization labyrinth environment 1200 that utilizes a carousel-based baffles in accordance with an illustrative embodiment of the present invention. A sterilization carousel 705 accepts bottles from a input carousel 1210 and discharges bottles onto a discharge carousels 1215. Input carousel 1210 may accept bottles from additional carousels 1205. Similarly, discharge carousel 1215 made offload bottles to additional output carousels 1220. Illustratively, the input and output carousels 1210, 1215 include a plurality of baffles 1225 that extend radially from a center of the carousel. The baffles 1225 provide additional shielding between bottles to further reduce the amount of radiation that may be released in environment 1200. Illustratively, the baffles 1225 do not necessarily need to extend all the way to an outer wall of carousels 1210, 1215. As long as the baffles 1225, which are illustratively comprised of appropriately shielded materials, are of a sufficient size to reduce the possibility of x-rays escaping from sterilization chamber to unshielded areas without requiring three reflections.

Figure 13:
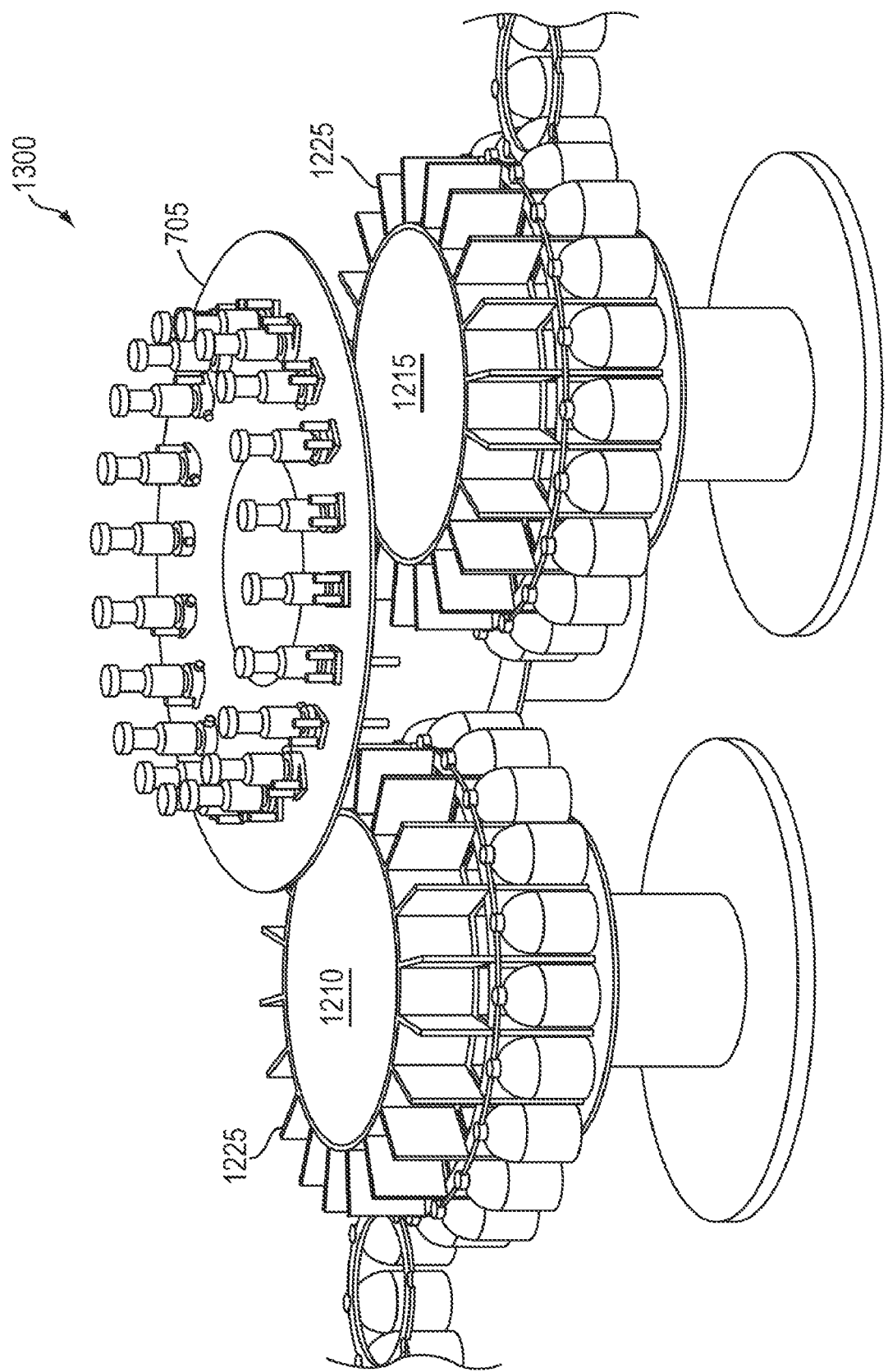
FIG. 13 is a cutaway view of an exemplary enclosed electron beam sterilization environment utilizing baffles in accordance with an illustrative embodiment of the present invention.

FIG. 13 is a cutaway view of an exemplary enclosed electron beam sterilization environment 1300 utilizing baffles in accordance with an illustrative embodiment of the present invention. As can be seen in exemplary environment 1300, input and output carousels 1210, 1215 include baffles 1225 that extend above and below the height of bottles being sterilized. Additionally, carousels 1210, 1215 include appropriate gripping mechanisms between each baffle to maintain bottle placement and positioning. It should be noted that in alternative embodiments additional and/or differing transport mechanisms may be utilized. As such, the illustration of gripping mechanisms being utilized for conveying bottles along carousels should be taken as exemplary only.

Figure 14:
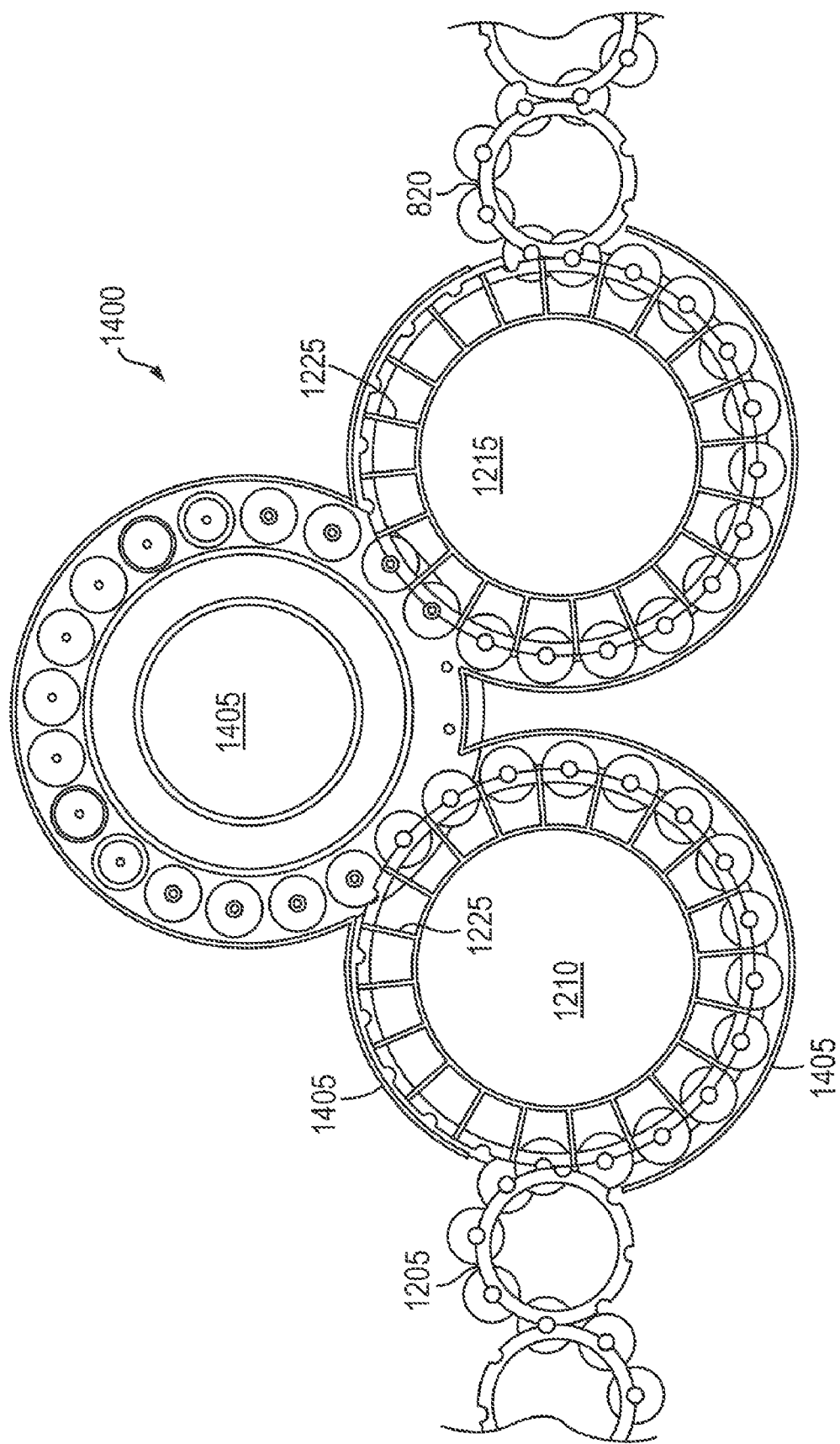
FIG. 14 is a schematic diagram of an exemplary enclosed electron beam sterilization environment utilizing baffles in accordance with an illustrative embodiment of the present invention.

FIG. 14 is a schematic diagram of an exemplary enclosed electron beam sterilization environment 1400 utilizing baffles in accordance with an illustrative embodiment of the present invention. In this view 1400, baffles 1225 extend further radially than that shown in exemplary environment 1200 above. In such an environment 1400, shielding 1405 may be placed along the exterior of the sterilization carousel and the input and output carousels 1210, 1215. As will be appreciated by one skilled in the art, by utilizing baffles along the interior of carousels, the number of potential reflection angles is reduced, thereby substantially reducing the shielding required to ensure that the x-ray radiation that escapes from the shielded environment has reflected at least three times.

Figure 15:
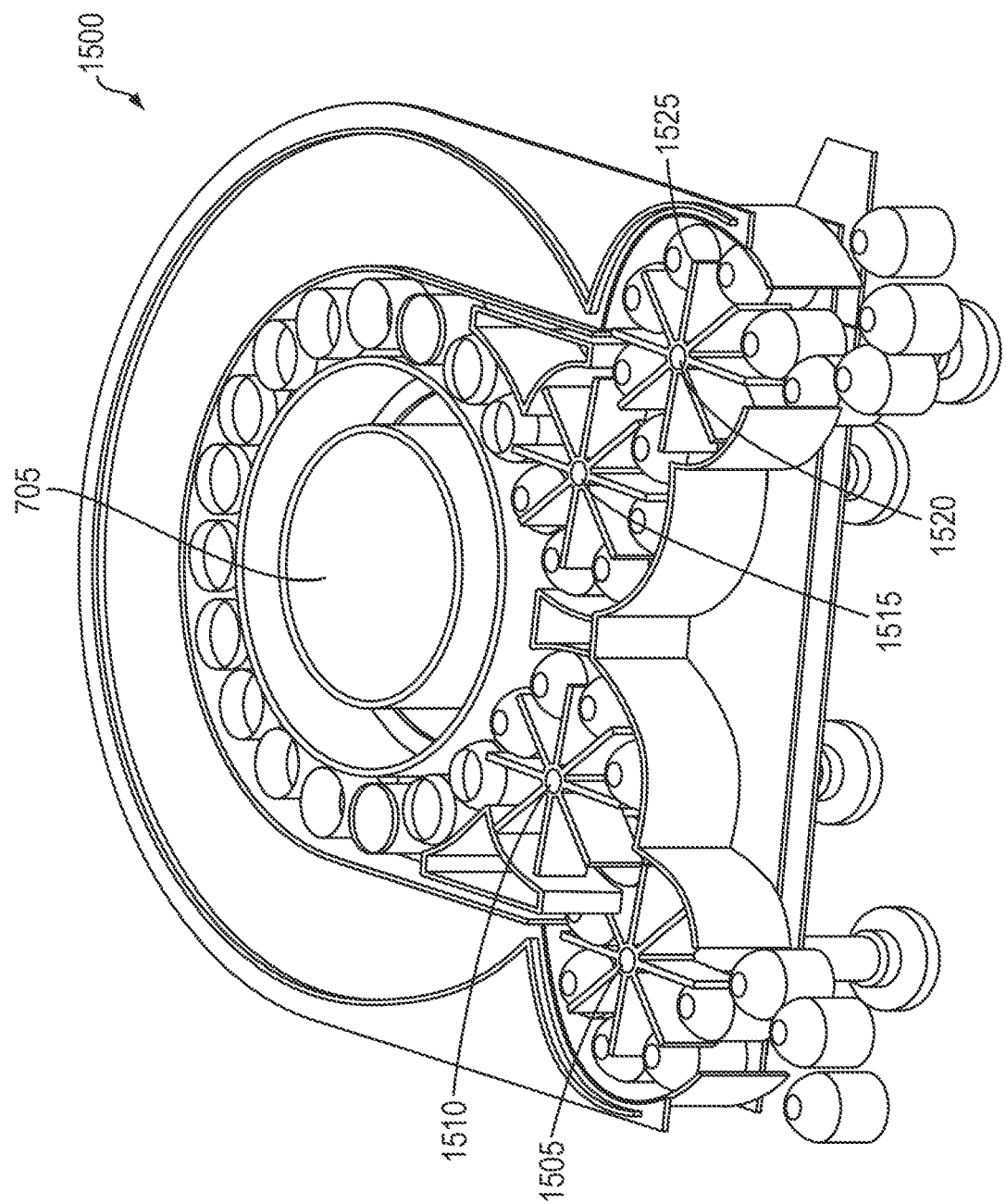
FIG. 15 is a cutaway view of an exemplary enclosed electron beam sterilization environment utilizing baffles in accordance with an illustrative embodiment of the present invention.

FIG. 15 is a cutaway view of an exemplary enclosed electron beam sterilization environment 1500 utilizing baffles in accordance with an illustrative embodiment of the present invention. Sterilization carousel 705 is operatively interconnected with a first and second input carousels 1505, 1510 as well as first and second discharge carousels 1515, 1520. It should be noted that the description of the two input and/or discharge carousels to be taken as exemplary only. It is expressly contemplated that in alternative embodiments of the present invention, a varying number of input/output carousels may be utilized. Carousels 1505, 1510, 1515 and 1520 illustratively each include a plurality of baffles 1225. In alternative embodiments of the present invention, the baffles 1225 may be configured so that they overlap with baffles 1225 from an adjacent carousel. That is, baffles 1225 on carousels 1505, 1510 overlap as the carousels rotate. Similarly, baffles 1225 on carousels 1515, 1520 may overlap. This may be utilized to provide additional shielding and further reduce amounts of x-ray radiation emitted.

Figure 16:
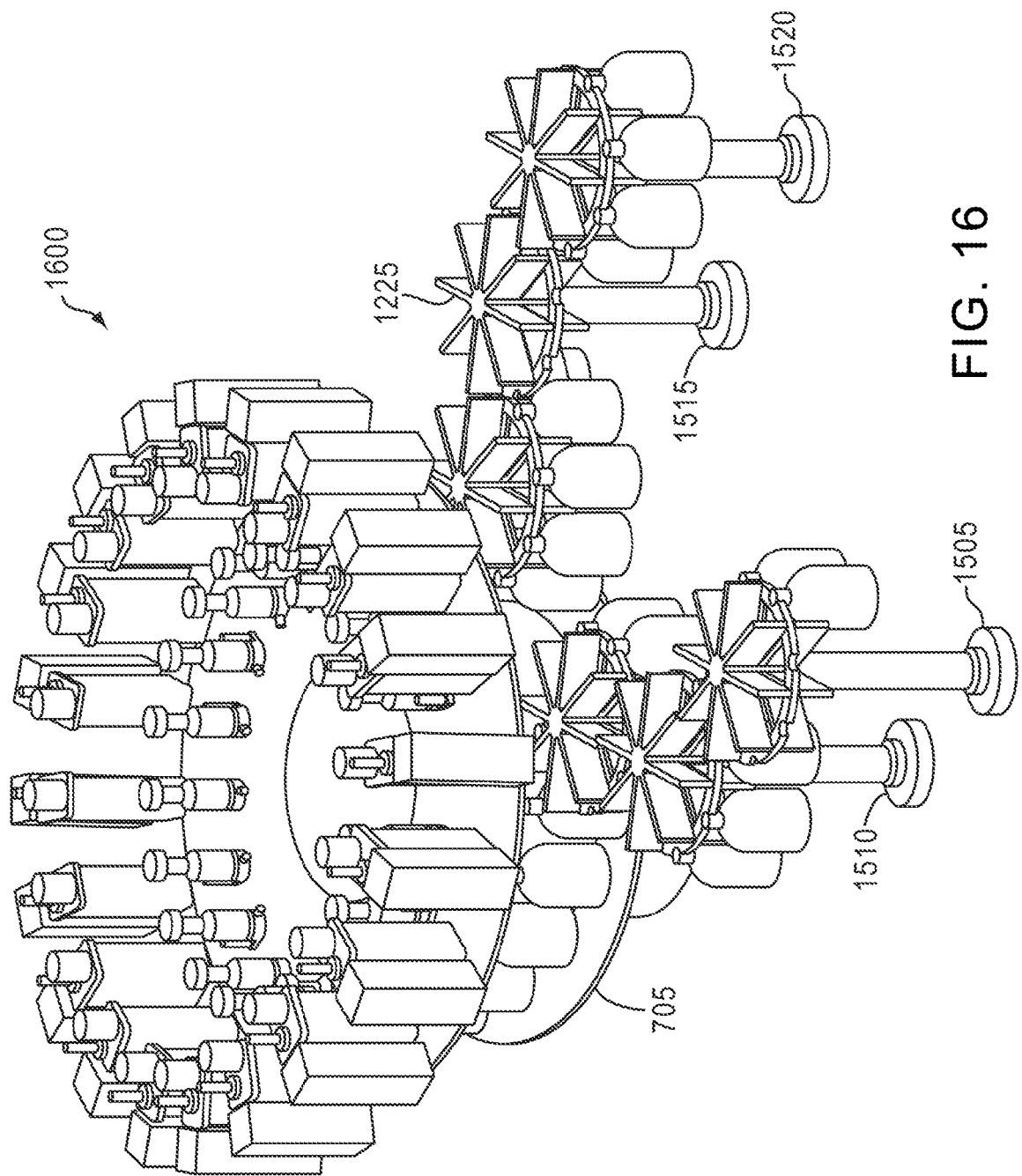
FIG. 16 is a cutaway view of an exemplary enclosed electron beam sterilization environment utilizing baffles in accordance with an illustrative embodiment of the present invention.

FIG. 16 is a cutaway view of an exemplary enclosed electron beam sterilization environment 1600 carousel utilizing baffles in accordance with an illustrative embodiment of the present invention. As can be seen from environment 1600, baffles 1225 extend above the level of bottles and provide obstructions for potential electron beam radiation. As noted above, in alternative embodiments of the present invention, baffles 1225 may be aligned so that they overlap during operation. That is, baffles 1225 on carousels 1505, 1510 may overlap, thereby providing additional security against spurious x-ray radiation. However, it should be noted that overlapping of baffles is not required. Baffle size may be selected by a manufacturer to ensure that x-ray radiation paths are limited in accordance with the principles of the present invention.

Figure 17:
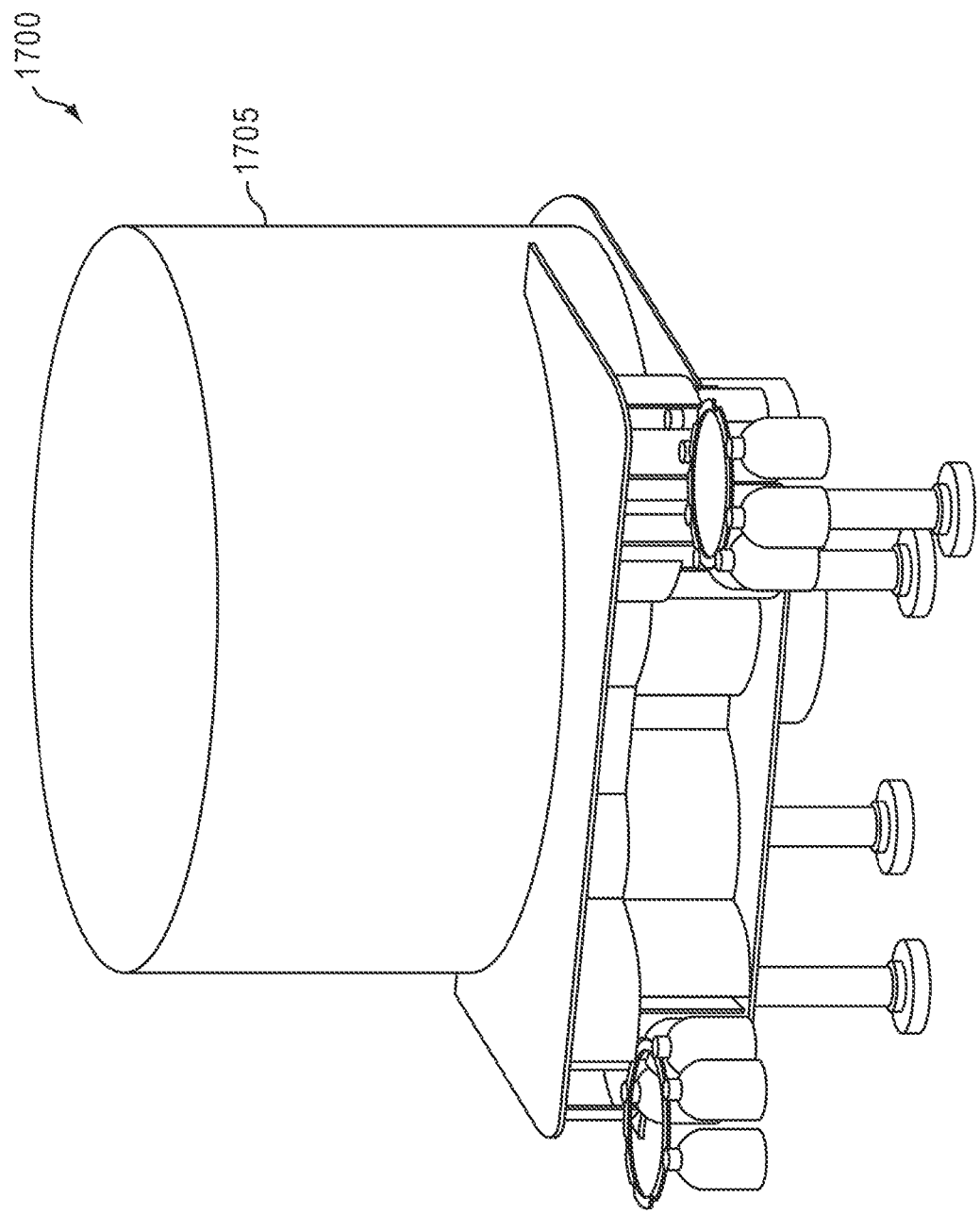
FIG. 17 is a view of an exemplary enclosed electron beam sterilization environment utilizing baffles in accordance with an illustrative embodiment of the present invention.

FIG. 17 is a perspective view of an exemplary enclosed electron beam sterilization environment 1700 utilizing baffles in accordance with an illustrative embodiment of the present invention. As can be seen in this perspective view of environment 1700, shielding 1705 to be placed over electron beam the emitters and power supplies. As discussed above in relation to FIG. 11, shielding 1705 may be removable. The shielding 1705 may be removed to enable maintenance and/or repair of electron beam the mentors and/or power supplies and associated apparatus. Furthermore, a maintenance hatch (not shown) may be installed on shielding 1705 to enable easy access for repair without requiring removal of the entire shielding mechanism 1705.

Figure 18:
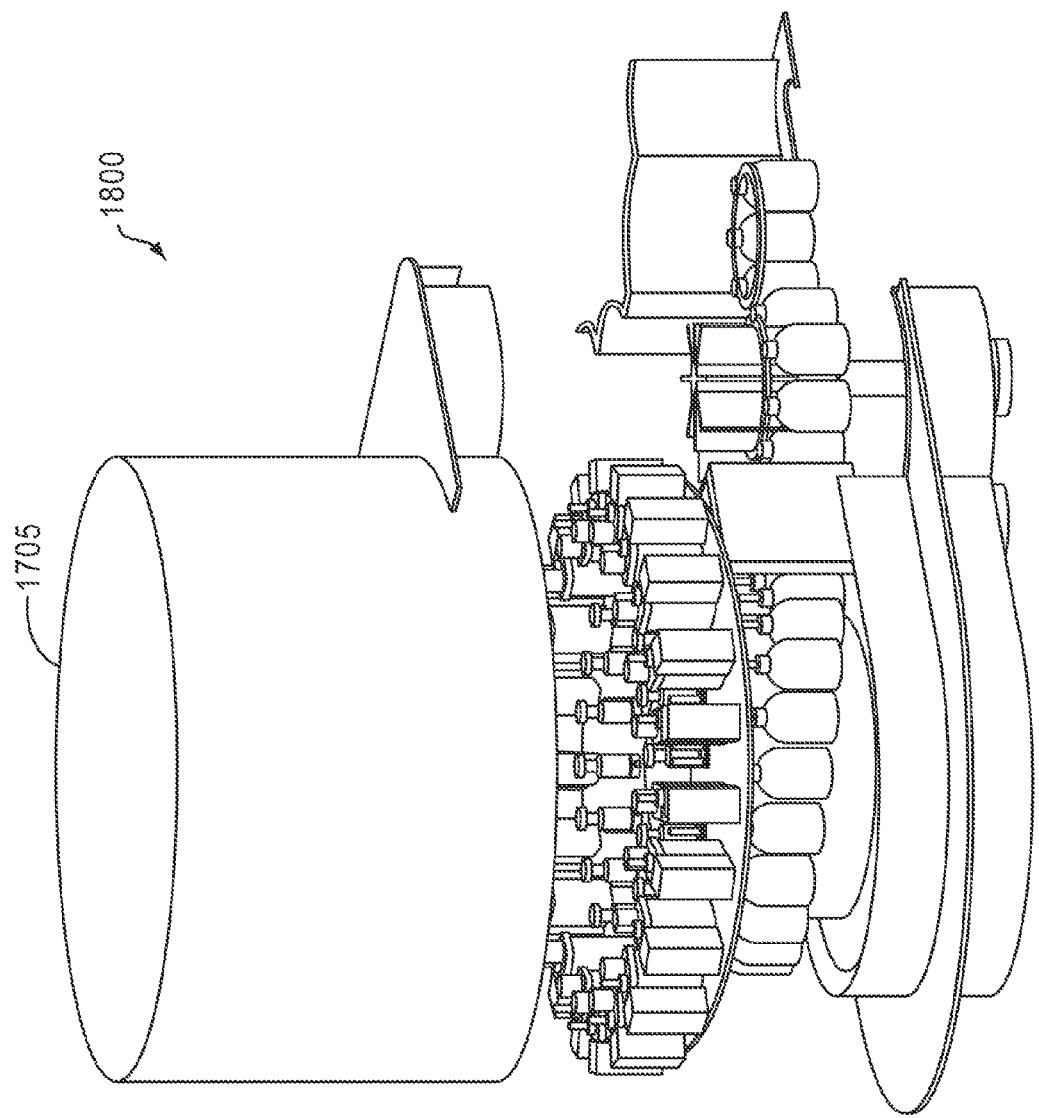
FIG. 18 is an exploded view of an exemplary enclosed electron beam sterilization environment showing removable shielding in accordance with an illustrative embodiment of the present invention.

FIG. 18 is exploded view of an exemplary enclosed electron beam sterilization environment 1800 showing removable shielding in accordance with an illustrative embodiment of the present invention. Environment 1800 illustrates shielding 1705 being removed. As noted above, shielding 1705 may be removed for maintenance and/or repair operations.

Figure 19:
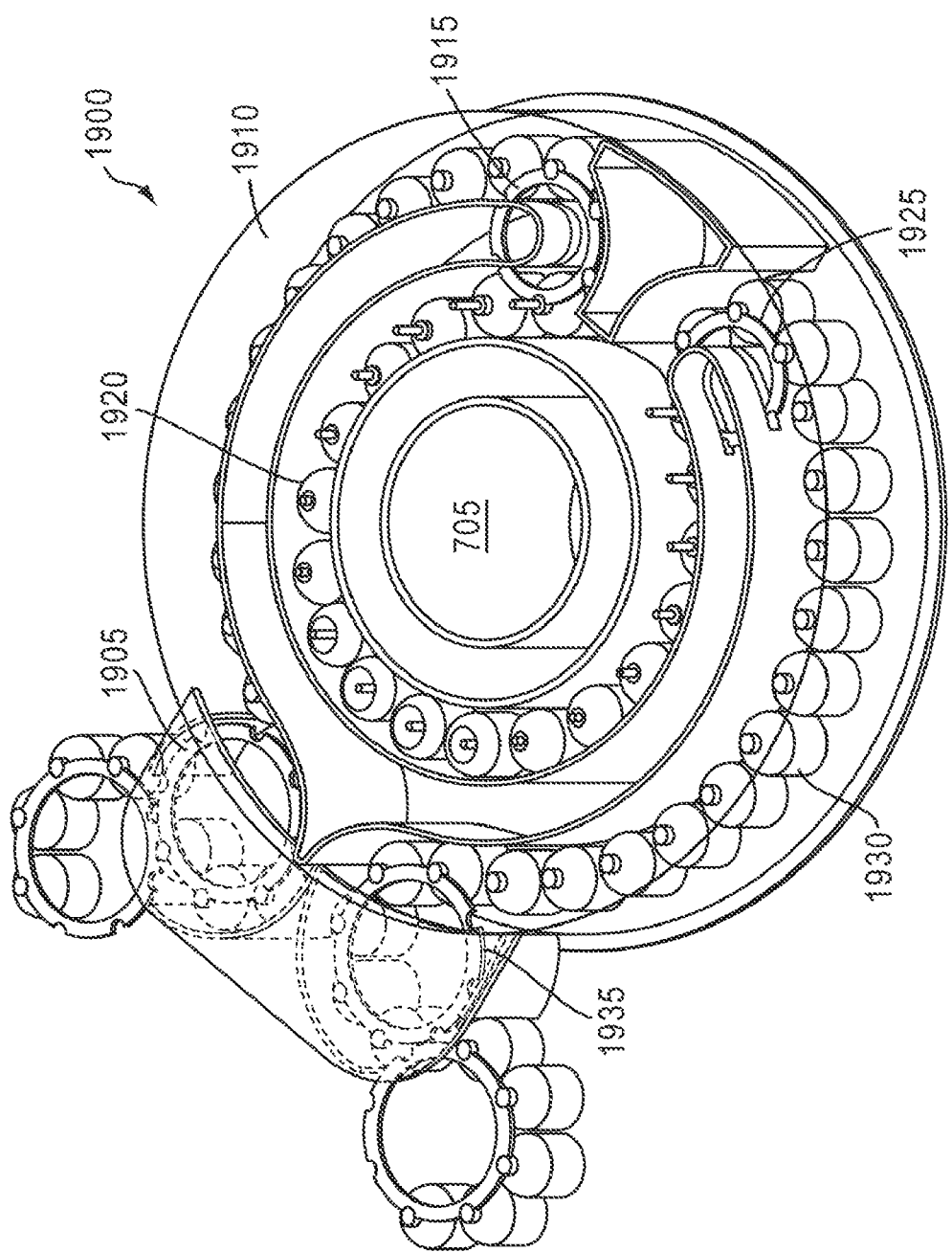
FIG. 19 is an exemplary view of an exemplary enclosed electron beam double labyrinth sterilization environment in accordance with an illustrative embodiment of the present invention.

FIG. 19 is a top view of an exemplary enclosed electron beam double labyrinth sterilization environment 1900 in accordance with an illustrative embodiment of the present invention. Environment 1900 includes a sterilization carousel 705 that is surrounded by an enclosed input labyrinth 1910 that is surrounded by an enclosed input labyrinth 1910. The input labyrinth 1910 receives bottles from a set of input carousels 1905. An interior labyrinth carousel 1915 moves bottles from the exterior input labyrinth 1910 into the interior of the sterilization carousel 705. Output carousels 1925 takes bottles from the sterilization carousel 705 and moves them to the exterior discharge labyrinth 1930. Bottles are then removed onto output carousels 1935.

Figure 20:
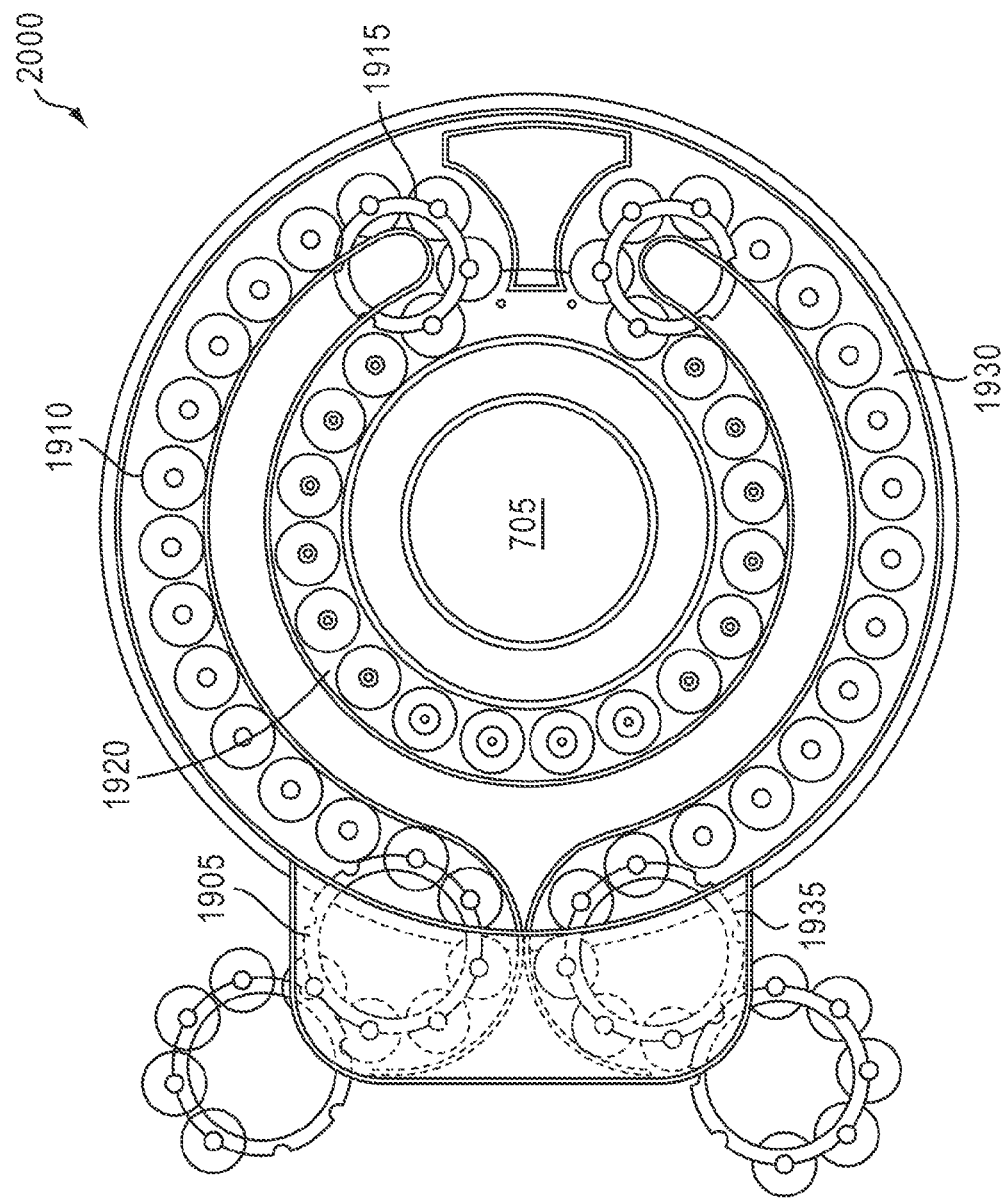
FIG. 20 is a schematic diagram of an exemplary electron beam sterilization apparatus in accordance with an illustrative embodiment of the present invention.

FIG. 20 is a top view of an exemplary double labyrinth sterilization carousel environment 2000 in accordance with an illustrative embodiment of the present invention. Environment 2000 corresponds to environment shown in FIG. 19. As will be appreciated by one skilled in the art, by maintaining the sterilization carousel 705 within an interior labyrinth, the chance of spurious emission of radiation is further reduced. The double labyrinth design may be utilized as a technique to save production of floor space in alternative embodiments of the present invention.

Figure 21:
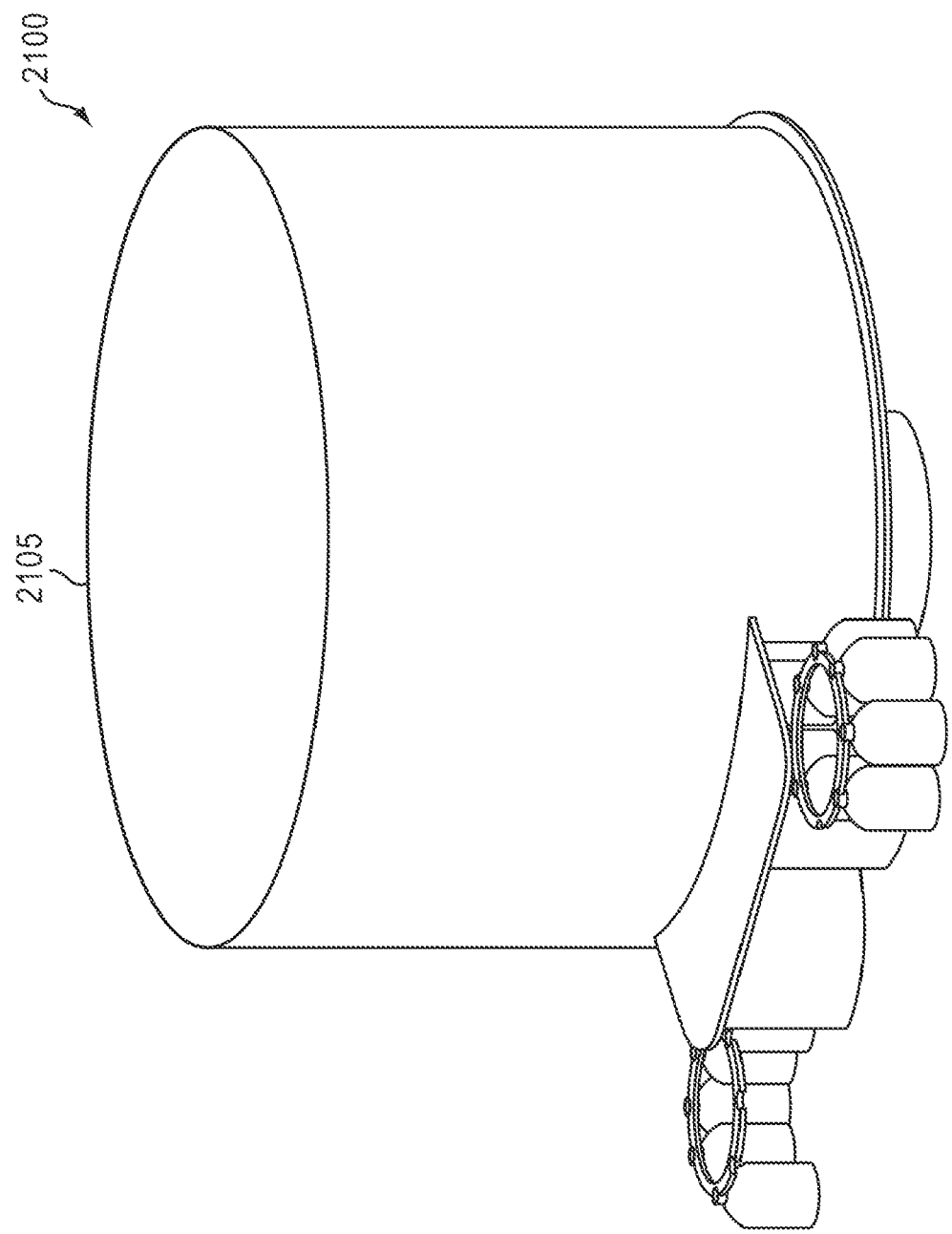
FIG. 21 is a schematic diagram of an exemplary electron beam sterilization apparatus showing a shielding cover in accordance with an illustrative embodiment of the present invention.

FIG. 21 is a perspective view of an exemplary double labyrinth sterilization carousel environment 2100 illustrating exterior shielding in accordance with an illustrative embodiment of the present invention. Environment 2100 includes exterior shielding 2105. As can be appreciated from the perspective view of environment 2100, the shielding covers the electron beam emitter power supplies and electron beam emitters as was the enclosed double labyrinth. It should be noted that in alternative embodiments of the present invention, shielding 2105 may be removable to enable maintenance and/or repair operations to occur on electron beam the emitters and/or power supplies and related apparatus. Furthermore, in alternative embodiments, a maintenance hatch may be provided to enable easy access for repair operations.

Figure 22:
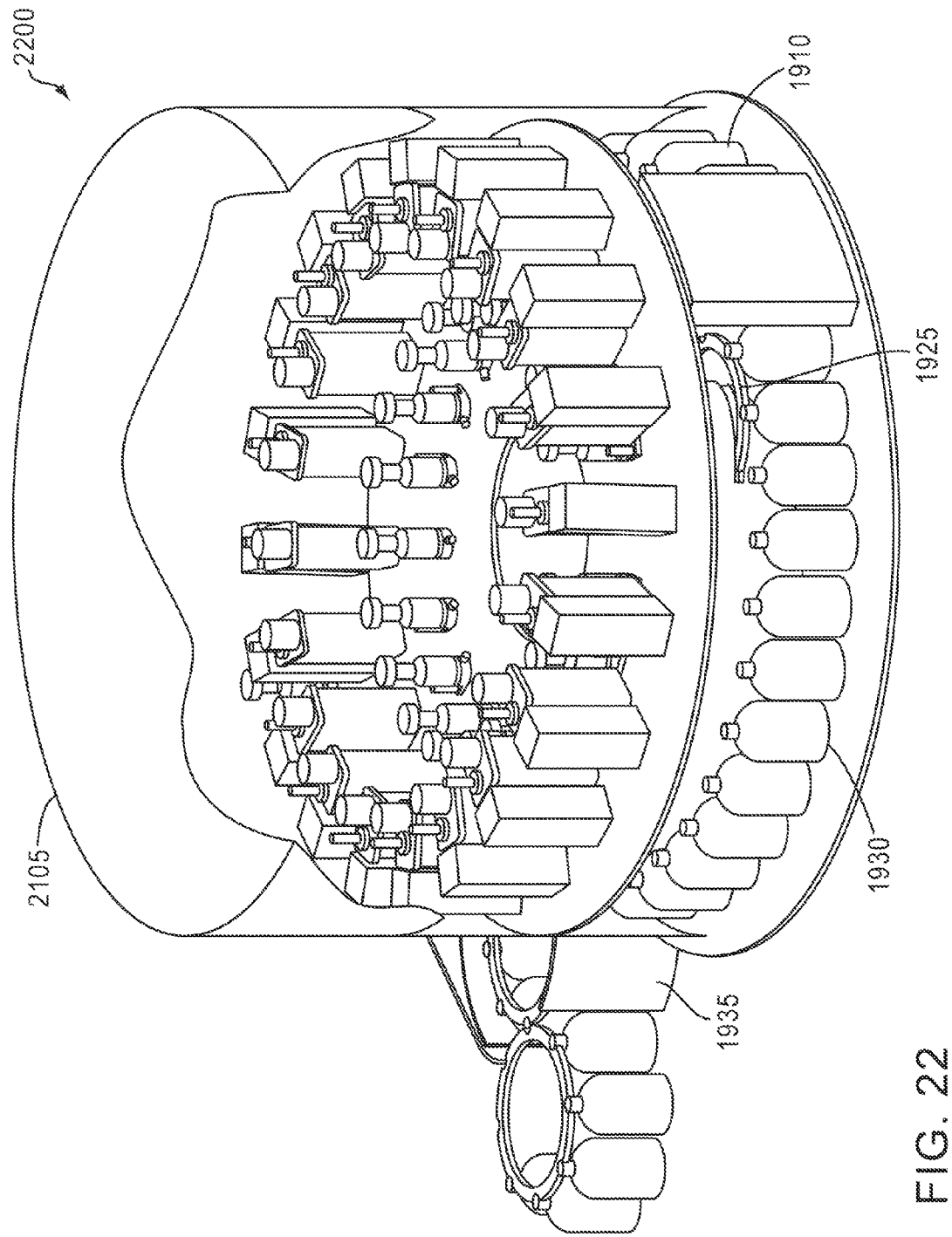
FIG. 22 is a cutaway view of an exemplary double labyrinth sterilization system in accordance with an illustrative embodiment of the present invention.

FIG. 22 is a perspective view of an exemplary double labyrinth sterilization carousel environment 2200 in accordance with an illustrative embodiment of the present invention. Environment 2200 illustrates a cutaway view of the shielding 2105 to illustrate the placement of electron beam emitter power supplies under the shielding. As noted above, in alternative embodiments, the shielding 2105 may be removable to enable repair and/or maintenance operations to occur. Similar or furthermore, in alternative embodiments a maintenance hatch (not shown) may be placed on shielding 2105 to enable the more routine maintenance to occur.

G. Electron Beam Radiation Paths in Shielded Enclosures

Typically, to ensure that x-ray radiation is not hazardous for humans, x-rays must be reflected/refracted at least three times to ensure that they are attenuated sufficiently. Thus, it is desirable to design shielding systems so that x-rays must be reflected at least three times to escape from the shielded enclosure. In such designs, any radiation that escapes from the enclosure is typically at such an attenuated level that does not provide health risks for humans. FIGS. 23-26 illustrate various radiation paths to escape from shielded enclosures in accordance with various embodiments of the present invention. As shown in the below-described figures, each of the shielding arrangements described herein require a minimum of three x-ray reflections to escape from a shielded region, thereby ensuring that humans are not harmed during sterilization operations.

Illustratively, for each of the alternative embodiments described herein, analysis may be performed to identify worst case scenarios to ensure that shielding is extended to provide the desired level of attenuation. By worst case it is generally meant, angles of reflection that are most advantageous to x-ray radiation to escape from the shielded region of a sterilization environment.

Figure 23:
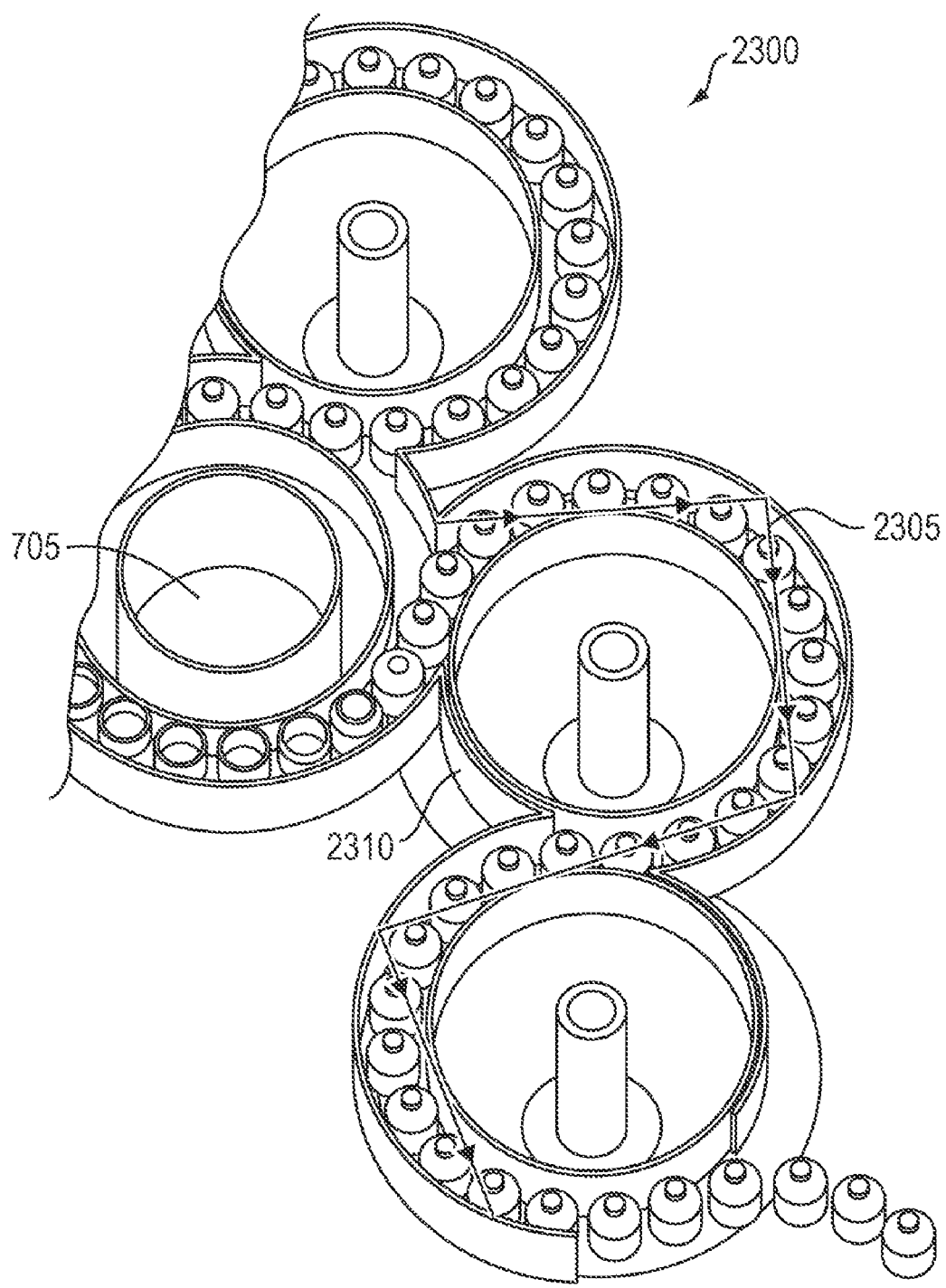
FIG. 23 is a view illustrating potential x-ray radiation reflection paths in accordance with an illustrative embodiment of the present invention.

FIG. 23 is a view illustrating potential x-ray radiation reflection paths in accordance with an illustrative embodiment of the present invention. Environment 2300 is associated with an exemplary system utilizing an enclosed carousel for input/discharge, described above in relation to FIG. 7. As can be seen in environment 2300, exemplary x-ray radiation path 2305 originates within the sterilization carousel 705 and requires at least reflections to escape from the shielded region. As noted above, by analyzing the worst case radiation reflection paths, a determination can be made on how to minimize shielding in alternative embodiments of the present invention.

Figure 24:
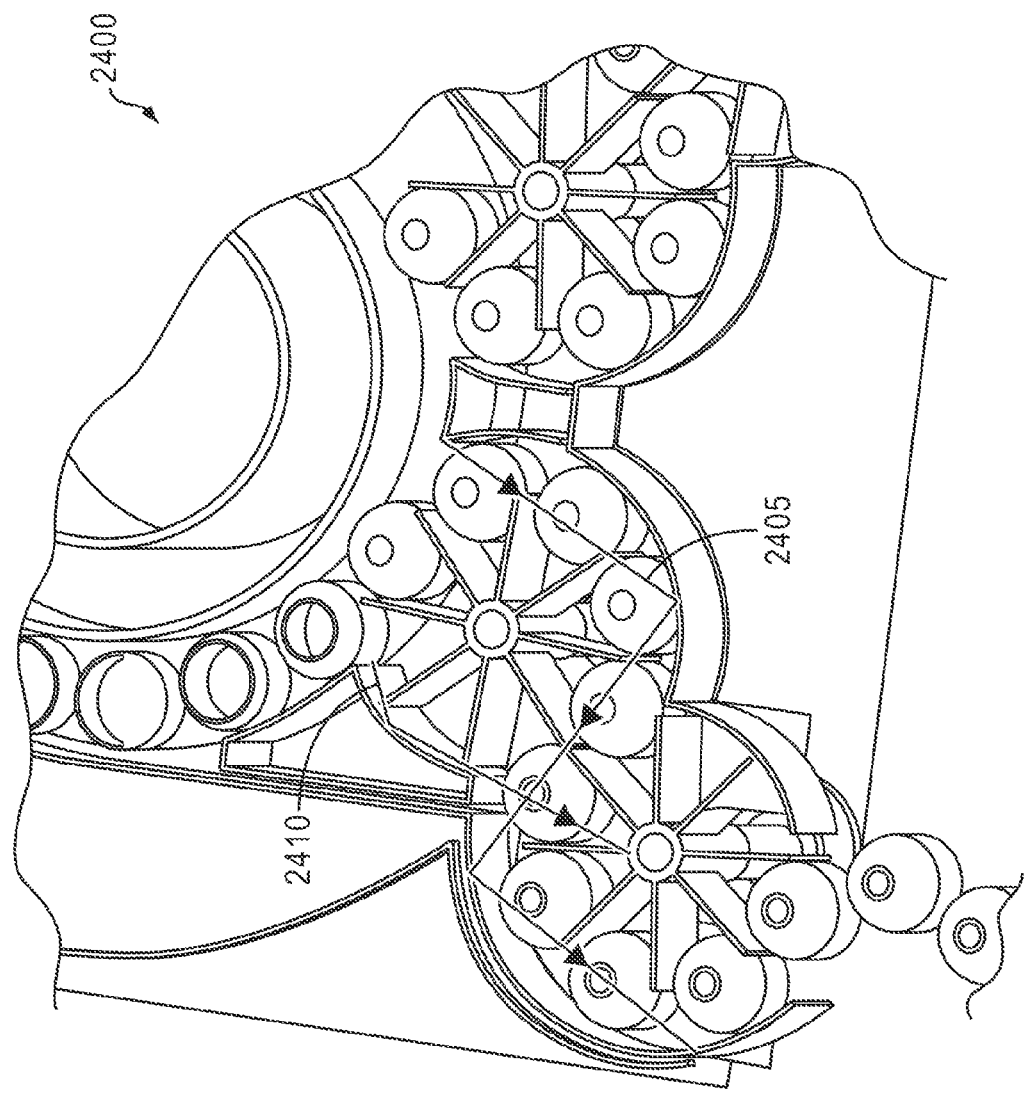
FIG. 24 is a view illustrating potential x-ray radiation reflection paths in accordance with an illustrative embodiment of the present invention.

FIG. 24 is a view illustrating potential x-ray radiation reflection paths in accordance with an illustrative embodiment of the present invention. Environment 2400 is associated with an exemplary system utilizing dual baffle carousels for input/discharge, described above in relation to FIG. 15. As can be seen in environment 2400, exemplary x-ray radiation path 2405 originates within the sterilization carousel and requires at least reflections to escape from the shielded region. As noted above, by analyzing the worst case radiation reflection paths, a determination can be made on how to minimize shielding in alternative embodiments of the present invention.

Figure 25:
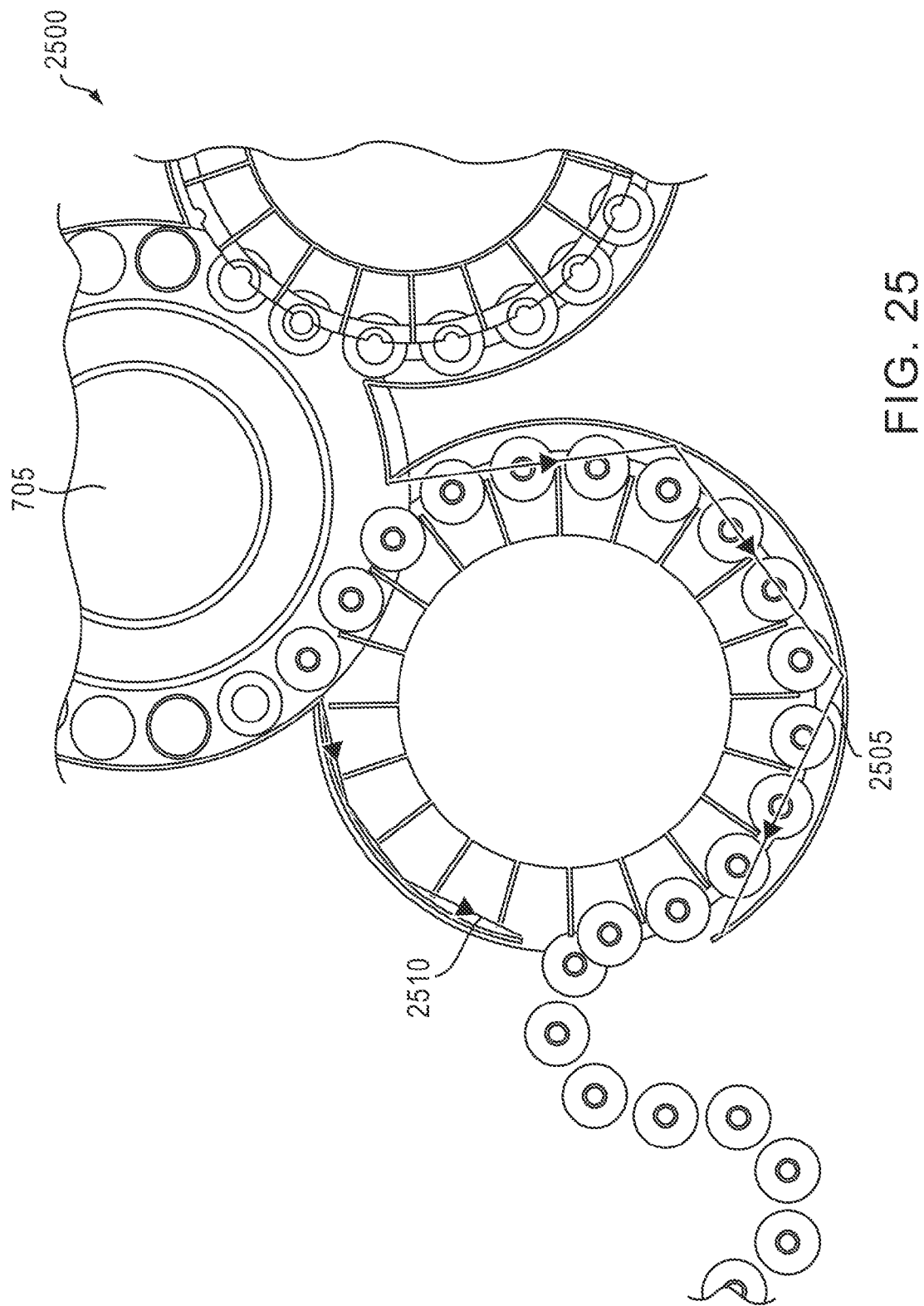
FIG. 25 is a view illustrating potential electron beam radiation reflection paths in accordance with an illustrative embodiment of the present invention.

FIG. 25 is a diagram illustrating potential x-ray radiation paths in accordance with an illustrative embodiment of the present invention. Environment 2100 is associated with an exemplary system utilizing a single baffle fielded carousel for input/discharge, described above in relation to FIG. 12. As can be seen in environment 2500, exemplary x-ray radiation path 2505 originates within the sterilization carousel and requires at least reflections to escape from the shielded region. As noted above, by analyzing the worst case radiation reflection paths, a determination can be made on how to minimize shielding in alternative embodiments of the present invention.

Figure 26:
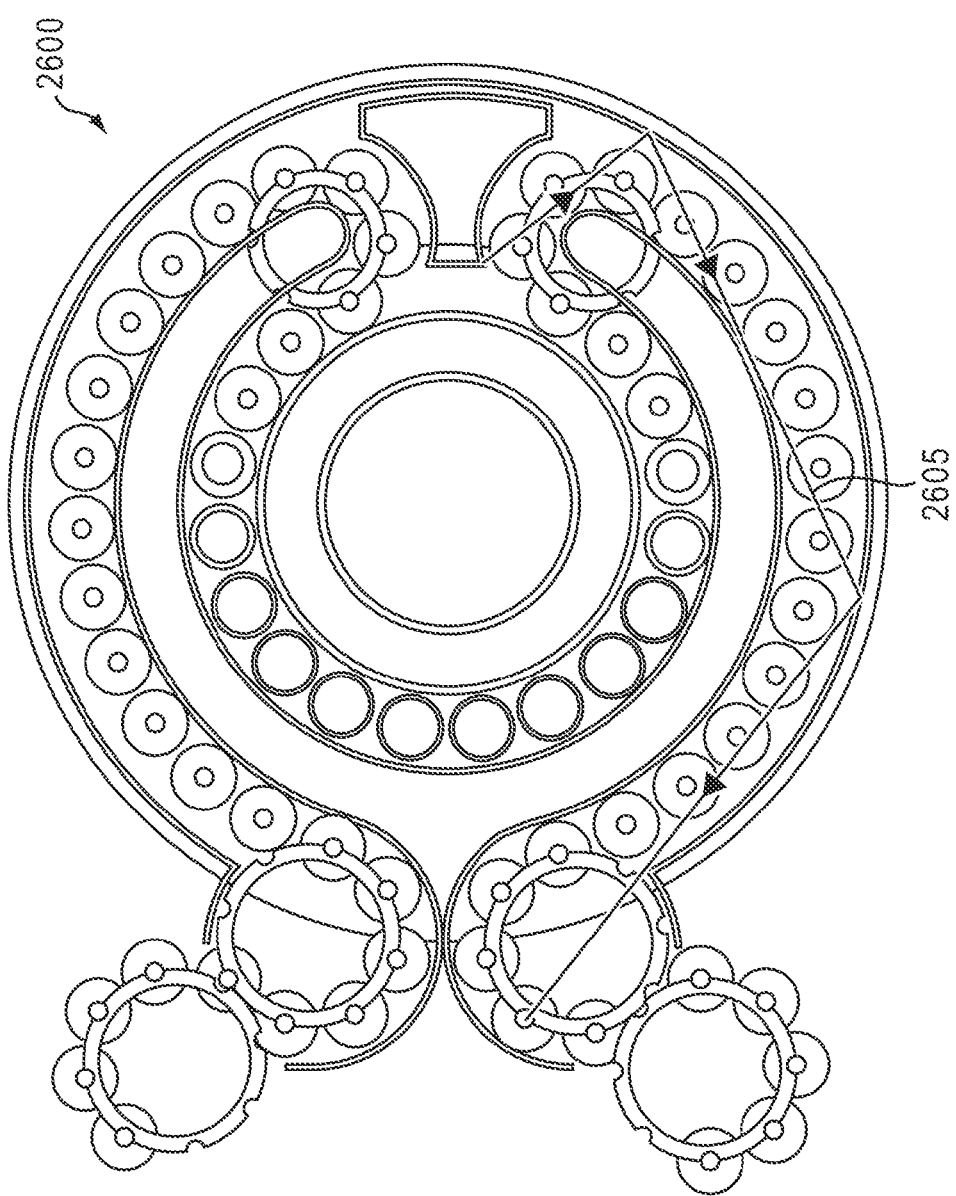
FIG. 26 is a view illustrating potential electron beam radiation paths in accordance with an illustrative embodiment of the present invention.

FIG. 26 the view illustrating potential x-ray radiation paths in accordance with an illustrative embodiment of the present invention. Environment 2600 is associated with an exemplary double labyrinth system, described above in relation to FIG. 19. As can be seen in environment 2605, exemplary x-ray radiation path 2205 originates within the sterilization carousel and requires at least reflections to escape from the shielded region. As noted above, by analyzing the worst case radiation reflection paths, a determination can be made on how to minimize shielding in alternative embodiments of the present invention.

Certain changes may be made in implementing the novel shielding techniques set forth, it is intended that all matter contained in the above description or shown in the accompanying drawings shall be interpreted as illustrative and not in a limiting sense. Furthermore, while this description has been written in terms of performing in the bottle (ITB) sterilization, the principles of the present technique may be utilized for sterilization of any non-web-based material including, for example exterior sterilization of bottles or other packaging materials. Additionally, while this description is written in terms of x-ray sterilization, the principles of the present invention may be utilized for other radiation-based sterilization techniques. Similarly, while the description of x-ray requiring at least three reflections to be attenuated to be safe for humans, the principles of the present invention are expressly contemplated to cover varying numbers of necessary reflections. As such, the description of the three reflections contained herein should be considered an exemplary only.

H. Sterilization of Deep Hole Targets

Electron beam emitters have been used for many years to irradiate and sterilize various targets including the interiors of containers. These hollow targets may be characterized by their aspect ratio, that is the ratio of their opening size to the length of the target from the opening to the bottom or base. As the aspect ratio increases (that is the length increases relative to the opening), it requires greater and greater beam voltage to sterilize the interior surfaces along the full length and the bottom. This is due to the scattering of electrons in air as they collide with air molecules and travel transverse to the length of the container and are absorbed by the target wall. The "scatter length" is the distance the electron beam will travel through the hollow target before being substantially dispersed due to scattering. As the voltage of the beam increases, the scattering length increases. Since there are many advantages of low voltage (<150 kV) systems (e.g. less shielding, lower consumption, less packaging material damage, smaller size and expense), it is desirable to find solutions that overcome the scattering problem. This has usually been done in the following ways:

1. For hollow targets with low enough aspect ratios, electron beam emitters are positioned above the container and direct energy through the mouth thereof. Sufficient energy is absorbed on all interior surfaces of the container including the bottom as discussed in U.S. Pat. No. 3,780,308, the contents of which are hereby incorporated by reference.

2. For hollow targets with high aspect ratios or with a shape that prevents a beam fixed above the target from reaching all surfaces (e.g. for a bottle), the electron beam emitter is usually formed with a narrow nozzle that is dimensioned to project into the target volume through the mouth of the target as discussed in U.S. Patent Publication No. 2008/0073549A1, the contents of which are hereby incorporated by reference. The emitter is invariably positioned above the target, say, at a station of a rotary carousel so that the nozzle points down toward the target which may be supported by a vertically movable gripper. When it is time to irradiate the target, the gripper is raised up so that the target volume surrounds the nozzle. The emitter is then activated so that a beam of electrons emanating from a window at the distal end of the nozzle irradiates the interior surface of the target. The ebeam dose is of sufficient intensity, and lasts for a sufficient time, to sterilize the interior surfaces of the target.

In some cases, the hollow target may have a high enough aspect ratio to prohibit approach 1, but it is not possible or practical to employ approach 2.

In a separate, but related problem, if the target volume has an irregular shape, the lateral dispersion of the electron beam may not be sufficient to provide a sterilizing dose of radiation to all side walls of the target volume.

Some attempts have been made to alleviate the aforesaid problems by providing electromagnetic beam shaping or directing members outside the target which can steer the electron beam in a desired way; see e.g. U.S. Pat. No. 6,139,796, the contents of which are hereby incorporated by reference. However, such members take up critical space in the already crowded environment around the target being sterilized. U.S. Publication No. 2008/0073549 A1 teaches extending the range of an electron beam as it is projected into a target volume by introducing a low Z or light gas such as helium into the volume prior to activating the emitter. The interaction of the beam electrons with these lower density gas molecules results in a longer ebeam path than would be the case if the target volume were filled with air.

In practice, however, it has proven difficult to provide a selected gas environment within a target volume which remains stable and consistent throughout the sterilization cycle. For example, when the selected gas is piped into the target volume, that gas, being lighter than air, tends to rise up and escape through the open mouth of the container. This adverse effect is exacerbated because the target volume e.g., a bottle preform, is usually supported in a carousel or other such machine which is subjected to various scripted movements as well as to vibration.

Figure 27:
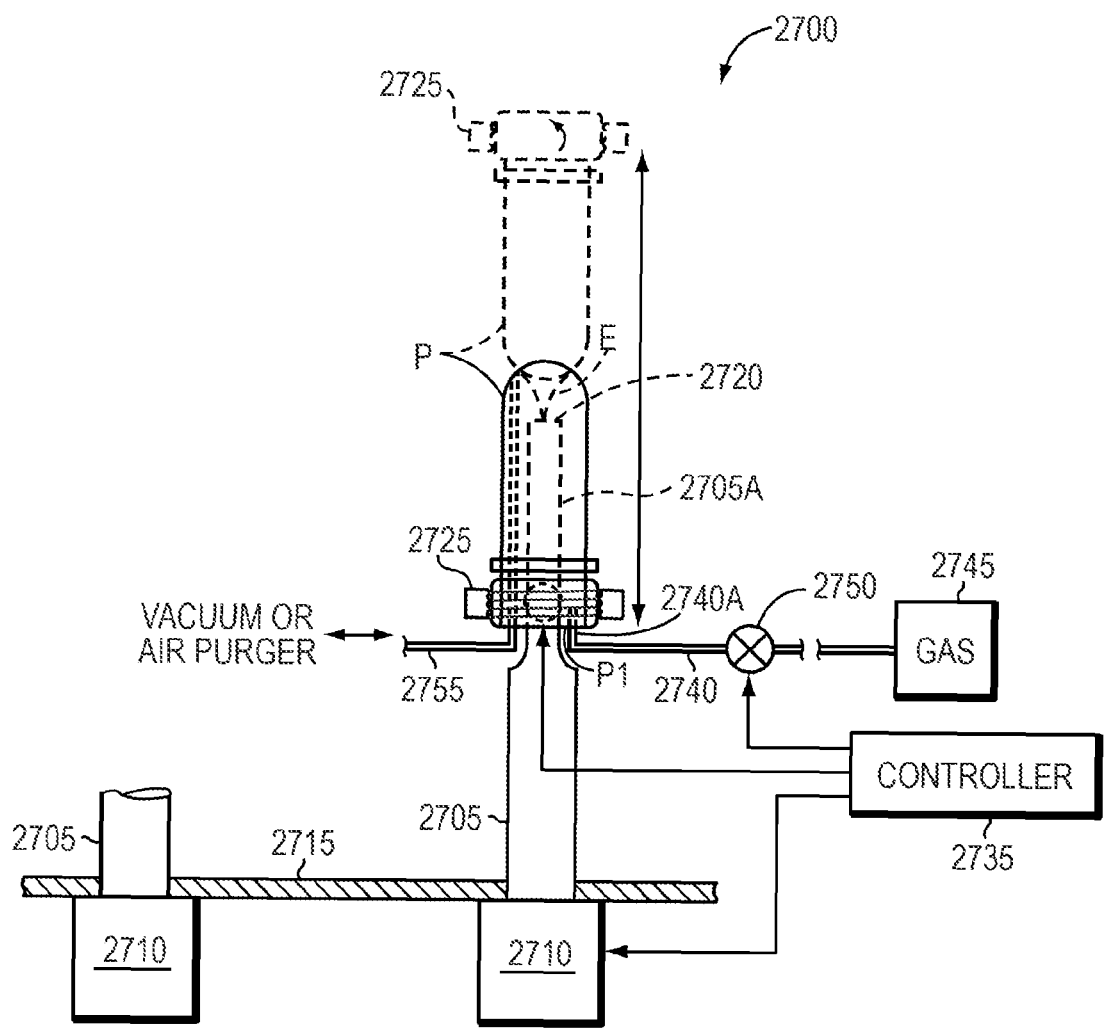
FIG. 27 is a schematic view of a system for controlling the degree of scattering of an ebeam projected into a target to achieve increased ebeam penetration in accordance with an illustrative embodiment of the present invention.

FIG. 27 shows an ebeam emitter 2705 having a narrow nozzle 2705A and a power supply 2710. Whereas such emitters are usually mounted so that the nozzle 2705A faces downward, emitter 2705 is supported by a support member 2715 so that its nozzle 2705A faces upward. For example, support member 2715 may be a carousel that supports a multiplicity of emitters 2705 distributed around the rotary axis of the carousel. Each emitter 2705 may be of the type described in U.S. Publication No. 2008/0073549A1, the contents of which are hereby incorporated herein by reference.

Suffice it to say here that emitter 2705 emits a beam of electrons e through a window 2720 at the distal end of nozzle 2705A.

Associated with each emitter 2705 is a gripper 2725 which is adapted to support a target to be irradiated. The illustrated target is a bottle preform P, but the target could just as well be a bottle or other relatively deep hollow article.

In any event, the gripper 2725 grips the finish of preform P and is adapted to be rotated by a rotary step motor 2730 under the control of a controller 2735 so that the preform is either upright or inverted. The motor and gripper are also movable vertically between an upper position shown in phantom in FIG. 27 wherein the preform is spaced above nozzle 2705A with its mouth $P_1$ facing upward and a lower position shown in solid lines in that same figure wherein the preform is inverted such that its mouth $P_1$ faces downward and the emitter nozzle 2705A extends into the preform. Mechanisms for moving gripper 2725 up and down are well known in the field of bottle-processing carousels.

Also associated with each emitter 2705 is a gas inlet pipe 2740 which extends from a source 2745 of a selected light gas such as helium. The distal end segment 2740A of pipe 2740 lies close to emitter nozzle 2705A so that when the gripper 2725 moves the preform P onto the nozzle 2705A, the pipe segment 52740A projects through the mouth $P_1$ of the preform as shown in 2700. The gas flow from supply 2745 to the preform may be regulated by a valve 2750 under the control of controller 2735.

After the preform P has been moved to its lower position shown in solid lines in environment 2700, controller 2735 may open valve 2750 for a selected time so that the light gas flows into, and completely fills, the interior of preform P. Since the selected gas is lighter than air, it rises to the closed upper end of the preform and displaces all of the air in the preform thus creating a uniform gaseous environment within the preform. Then, the controller 2735 may activate the power supply 2710 so that a beam of electrons e projects from the distal end of the emitter nozzle 2705A thereby sterilizing the interior surfaces of the preform. This may occur as the preform is moving vertically relative to the nozzle as is well known in the art.

After the sterilization step is completed, gripper 2725 may be activated to move preform P vertically to its upper position shown in phantom in environment 2700, after which motor so that the preform is rotated until its mouth $P_1$ faces upwards. The light gas inside the preform will thereupon rise up out of the preform to be replaced by ambient air.

Still referring to environment 2700, instead of rotating the preform in order to remove the selected gas following ebeam exposure, the preform may remain in its inverted position shown in solid lines and the selected gas purged from the interior of the preform by directing air under pressure through a tube 2755 that extends to the closed upper end of the preform. Alternatively, a vacuum may be drawn in the preform to achieve the same objective.

Figure 28:
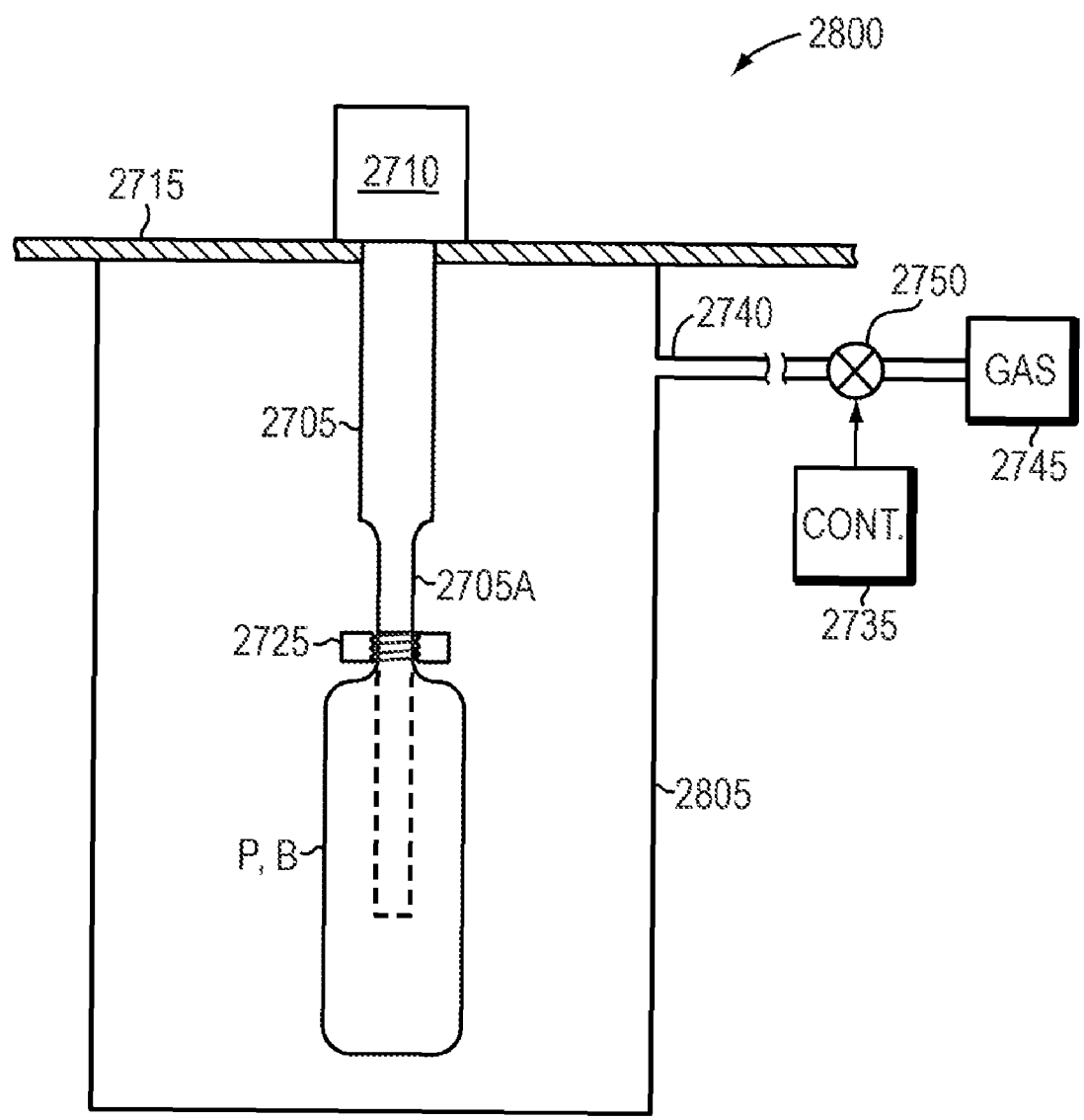
FIG. 28 is a schematic view of an alternative system for controlling the degree of scattering of an ebeam projected into a target to achieve increased ebeam penetration in accordance with an illustrative embodiment of the present invention.

Referring now to FIG. 28 which illustrates a second embodiment of the apparatus wherein the emitter 2705 and the target, e.g., a bottle preform P or bottle B, are operated in an environment that consists primarily of the selected gas. The components of environment 2800 that are more or less the same as those in environment 2700 carry the same identifying characters. In the environment 2800, the emitter/target combination are contained within a fluid-tight enclosure 2805. Enclosure 2805 may be local to each emitter/target pair or it may enclose an entire carousel containing many such pairs. In any event, the volume within enclosure 2805 may be filled with a selected gas which is piped into that space via a pipe 2740 connected to a gas supply 2745. The flow of gas through pipe 2740 may be regulated by a solenoid valve 2750 under the control of controller 2735.

If a particular application requires that the ebeam emitted by emitter 2705 have a maximum range in the target volume, the housing 2805 may be filled with a light or low Z gas such as helium. On the other hand, if the application requires that the ebeam projected into the target volume be dispersed laterally to a maximum degree, a high mass gas species such as Xenon may be injected into the housing 2805 so as to fill the target volume.

The foregoing description has been directed to particular embodiments of this invention. It will be apparent, however, that other variations and modifications may be made to the described embodiments, with the attainment of some or all of their advantages. For example, where electron beam treatment is described for the purposes of sterilization, it may also be for other purposes, e.g., curing of a coating, treating a surface, modifying the properties of the material such as crosslinking, for the purpose of improving chemical, mechanical, and/or thermal resistance properties. ITB sterilization techniques may be utilized with both rotary fill and linear fill line systems. In alternative embodiments, the same processes described herein as being utilized prior to filling may be used on containers that have been filled but not yet sealed. For example, in certain applications, it may be preferable to fill the container and then used an electron beam to sterilize the "headspace," i.e. the portion of the container that has not been filled with product. It should be noted that while the term sterilization has been used in this description, and where the term sterilization is taken to mean something highly specific, it may be replaced with alternative terms including, but not limited to disinfected, sanitized, microbial reduced, etc.

Additionally, the procedures, processes and/or modules described herein may be implemented in hardware, software, embodied as a computer-readable medium having program instructions, firmware, or a combination thereof. Therefore, it is the object of the appended claims to cover all such variations and modifications as come within the true spirit and scope of the invention.

The invention claimed is:

1. An apparatus for sterilizing a bottle, the apparatus comprising:
    a movable electron beam emitter comprising an elongated nozzle having an electron beam window at a lower end of the elongated nozzle;
    a plurality of grippers configured to raise and lower the bottle around the elongated nozzle;
    one or more stationary electron beam emitters configured to sterilize an exterior of the bottle; and
    a controller operatively interconnected with the plurality of grippers and the movable electron beam emitter, the controller configured to modulate an electron beam dose rate delivered by the movable electron beam emitter.

2. The apparatus of claim 1 wherein the controller modulates the electron beam dose rate delivered by the movable electron beam emitter by varying a speed at which the bottle is raised and lowered by the plurality of grippers.

3. The apparatus of claim 1 wherein the controller modulates the electron beam dose rate delivered by the movable electron beam emitter by varying a current associated with the movable electron beam emitter.

4. The apparatus of claim 1 wherein the plurality of grippers are configured on a carousal and the movable electron beam emitter comprises one of a plurality of movable electron beam emitters arranged to rotate in a synchronous manner with the carousal.

5. The apparatus of claim 1 wherein the controller is configured to, in response to detecting an arc event associated with the movable electron beam emitter, modify power to the movable electron beam emitter so that the bottle receives an electron beam dose that is within a predefined range.

6. The apparatus of claim 1 wherein the controller is configured to, in response to detecting an arc event associated with the movable electron beam emitter, modify a speed at which the grippers raise and lower the bottle around the movable electron beam emitter so that the bottle receives an electron beam dose that is within a predefined range.

7. The apparatus of claim 1 wherein the controller is configured to, in response to detecting an arc event associated with the movable electron beam emitter, modify current to the movable electron beam emitter so that the bottle receives an electron beam dose that is within a predefined range.

8. The apparatus of claim 1 further comprising one or more sensors operatively interconnected with the controller.

9. The apparatus of claim 8 wherein the one or more sensors are configured to detect an output level of the movable electron beam emitter.

10. The apparatus of claim 8 wherein the one or more sensors comprise electrical sensors.

11. The apparatus of claim 8 wherein the one or more sensors comprise thermal sensors.

12. The apparatus of claim 1 wherein the one or more stationary electron beam emitters are oriented so that the bottle does not need to be rotated to ensure that sterilization of the entire exterior of the bottle occurs.

13. An apparatus for sterilizing a plurality of bottles, the apparatus comprising:
    a plurality of movable electron beam emitters, each comprising an elongated nozzle having an electron beam window at a lower end of the elongated nozzle;
    a plurality of grippers configured to raise and lower the plurality of bottles around one of the elongated nozzles of the plurality of movable electron beam emitters;
    one or more stationary electron beam emitters configured to sterilize an exterior of the plurality of bottles; and
    a controller operatively interconnected with the plurality of grippers and the plurality of movable electron beam emitters, the controller configured to modulate an electron beam dose rate delivered by each of the plurality of movable electron beam emitters.

14. An apparatus for sterilizing a bottle, the apparatus comprising:
    means for generating an electron beam;
    means for raising and lowering the bottle around the means for generating the electron beam;
    means for sterilizing an exterior of the bottle; and
    means for modulating an electron beam dose rate delivered by the means for generating the electron beam.

15. The apparatus of claim 1 wherein the apparatus is configured to transfer the bottle into a sterile zone.

16. The apparatus of claim 15 wherein only an upper portion of the bottle within the sterile zone is sterilized.

17. The apparatus of claim 15 wherein the sterile zone is maintained with positive air pressure.

18. The apparatus of claim 15 wherein the bottle is removed from an electron beam plume emitted from the electron beam emitter while the bottle is within the sterile zone.

19. The apparatus of claim 8 wherein readings from the one or more sensors are compared to one or more baseline readings from the one or more sensors to confirm the efficiency of the electron beam emitter.

20. The apparatus of claim 1 wherein the bottle is filled before it is sterilized by the electron beam emitter.

* * * * *